United States Patent
Minor et al.

(10) Patent No.: US 12,428,495 B2
(45) Date of Patent: Sep. 30, 2025

(54) ANTIBODIES AGAINST YKL-40 AND USES THEREOF

(71) Applicant: BIO-Y A/S, Helsingør (DK)

(72) Inventors: Peter Minor, København Ø (DK); Peter Kristensen, Tranbjerg (DK)

(73) Assignee: BIO-Y A/S, Helsingør (DK)

( * ) Notice: Subject to any disclaimer, the term of this patent is extended or adjusted under 35 U.S.C. 154(b) by 0 days.

(21) Appl. No.: 18/140,972

(22) Filed: Apr. 28, 2023

(65) Prior Publication Data

US 2024/0360246 A1   Oct. 31, 2024

(51) Int. Cl.
*C07K 16/40* (2006.01)
*A61K 45/06* (2006.01)

(52) U.S. Cl.
CPC .............. *C07K 16/40* (2013.01); *A61K 45/06* (2013.01); *C07K 2317/31* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 8,053,563 B2 * | 11/2011 | Bonnichsen | A61P 35/00 530/387.9 |
| 11,498,978 B2 | 11/2022 | Kristensen | |
| 2012/0149882 A1 | 6/2012 | Bonnichsen | |
| 2019/0062457 A1 * | 2/2019 | Elias | A61P 35/04 |
| 2020/0262930 A1 | 8/2020 | Chupp et al. | |
| 2021/0347912 A1 * | 11/2021 | Kristensen | C07K 16/40 |

FOREIGN PATENT DOCUMENTS

| | | |
|---|---|---|
| WO | WO2021/049830 A1 | 3/2021 |
| WO | WO2021/216667 A2 | 10/2021 |
| WO | WO2023/072405 A1 | 5/2023 |

OTHER PUBLICATIONS

Harmsen et al. Properties, production, and applications of camelid single-domain antibody fragments. Appl Microbiol Biotechnol 77, 13-22 (2007). https://doi.org/10.1007/s00253-007-1142-2 (Year: 2007).*
Vishwakarma et al. VHH Structural Modelling Approaches: A Critical Review. International Journal of Molecular Sciences. 2022; 23(7):3721. https://doi.org/10.3390/ijms23073721 (Year: 2022).*
Pothin et al. Brain Delivery of Single-Domain Antibodies: A Focus on VHH and VNAR. Pharmaceutics. 2020; 12(10):937, https://doi.org/10.3390/pharmaceutics12100937 (Year: 2020).*
Faibish et al. A YKL-40-Neutralizing Antibody Blocks Tumor Angiogenesis and Progression: A Potential Therapeutic Agent in Cancers. Mol Cancer Ther; 10(5) May 2011 (Year: 2011).*

(Continued)

*Primary Examiner* — Amy E Juedes
*Assistant Examiner* — Hilary Ann Petrash
(74) *Attorney, Agent, or Firm* — Weston R. Gould; Dinsmore & Shohl LLP

(57) ABSTRACT

The present invention relates to antibodies capable of binding murine and/or human YKL-40, as well as to compositions comprising one or more such antibodies. The invention also relates to such antibodies for use in a method of treatment of various diseases, such as cancer alone or in combination with other anti-cancer agents.

16 Claims, 10 Drawing Sheets
Specification includes a Sequence Listing.

(56) References Cited

OTHER PUBLICATIONS

Francescone et al. Role of YKL-40 in the Angiogenesis, Radioresistance, and Progression of Glioblastoma. The Journal of Biological Chemistry vol. 286, No. 17, pp. 15332-15343, Apr. 29, 2011 (Year: 2011).*
Chen et al. Chitinase 3-Like-1 Expression in Colonic Epithelial Cells as a Potentially Novel Marker for Colitis-Associated Neoplasia. AJP. Vol 179, No. 3, 2011 (Year: 2011).*
Culang et al. The structural basis of antibody-antigen recognition. Front. Immunol., Oct. 8, 2013. Sec. B Cell Biology. vol. 4—2013 (Year: 2013).*
Kapingidza et al. (2020). Antigen-Antibody Complexes. In: Hoeger, U., Harris, J. (eds) Vertebrate and Invertebrate Respiratory Proteins, Lipoproteins and other Body Fluid Proteins. Subcellular Biochemistry, vol. 94. Springer, Cham. (Year: 2020).*
Lu and Jacob. Biosimilars: not simply generics. US Pharm. 2019; 44(6) (Generic Drugs suppl):36-39 (Year: 2019).*
Selmaj et al. Introducing the biosimilar paradigm to neurology: the totality of evidence for the first biosimilar natalizumab. BioDrugs (2024). https://doi.org/10.1007/s40259-024-00671-4 (Year: 2024).*
Chang et al. The Role of Chitinase-3-like Protein-1 (YKL40) in the Therapy of Cancer and Other Chronic-Inflammation-Related Diseases. Pharmaceuticals 2024, 17, 307. https://doi.org/10.3390/ph17030307 (Year: 2024).*
Christ, D., et al., Repertoires of aggregation-resistant human antibody domains, Protein Engineering, Design & Selection, 20(8): 413-416, Aug. 24, 2007.
Morrison et al., Chimeric human antibody molecules: Mouse antigen-binding domains with human constant region domains, Proc Natl Acad Sci USA, 81: 6851-6855, Nov. 1984.
Brockmann et al., Synthetic single-framework antibody library integrated with rapid affinity maturation by VL shuffling, Protein Eng Des Sel, 24:691-700, Jun. 16, 2011.
Böckelmann et al., Detection of doxorubicn, cisplatin and therapeutic antibodies in formalin fixed paraffin-embedded human cancer cells, Histochem Cell Biol., 153(5):367-377, Mar. 3, 2020.

Fellhouse et al., High-throughput generation of synthetic antibodies from Highly Functional Minimalist Phage-displayed Libraries, J Mol Biol, 373: 924-940, Aug. 19, 2007.
Ferretti et al., Tumor interstitial fluid pressure as an Early-Response Marker for Anticancer Therapeutics, Neoplasia, 11(9):874-81, Sep. 2009.
Hust et al., Mating antibody phage display proteomics, Trends Biotechnol., 22(1): Jan. 8-14, 2004.
Jones et al., Replacing the complementarity-determining regions in a human antibody with those from a mouse, Nature, 321: 522-525, May 29, 1986.
Karahan et al., TCR-NK Cells: A Novel Source for Adoptive Immunotherapy of Cancer, Turk J Haematol., 40(1):1-10, Jan. 31, 2023.
Mandrup et al., A novel heavy domain antibody library with functionally optimized complementarity determining regions, PLoS One, 8(10): e76834., Oct. 8, 2013, 15 pages.
Melero et al., Evolving synergistic combinations of targeted immunotherapies to combat cancer, Nat Rev Cancer, 15: 457-472, Aug. 2015.
Moutel, S. et al., A multi-Fc-species system for recombinant antibody production, BMC Biotechnol., 9(14), Feb. 26, 2009, 9 pages.
Pansri et al., A compact phage display human scFv library for selection of antibodies to a wide variety of antigens, BMC Biotechnol, 9:6, Jan. 29, 2009, 16 pages.
Rothe et al., The human combinatorial antibody library HuCAL GOLD combines diversification of all six CDRs according to the natural immune system with a novel display method for efficient selection of high-affinity antibodies, J Mol Biol, 376: 1182-1200, 2008.
Silacci et al., Design, construction, and characterization of a large synthetic human antibody phage display library. Proteomics, 5: 2340-2350, 2005.
Wang et al., Design and Production of Bispecific Antibodies, Antibodies, 8, 43, Aug. 2, 2019, 30 pages.
Høgdall, E. et al., YKL-40 tissue expression and plasma levels in patients with ovarian cancer, BMC Cancer, Biomed Central, 9(1): pp. 1-10, Jan. 9, 2009.
Rudikoff, S. et al., Single amino acid substitution altering antigen-binding specificity, Proc. Natl Acad. Sci. USA, 79: 1979-1983, Mar. 1, 1982.

* cited by examiner

SEQUENCE LISTING

```
Sequence total quantity: 62
SEQ ID NO: 1              moltype = AA   length = 383
FEATURE                   Location/Qualifiers
source                    1..383
                          mol_type = protein
                          organism = Homo sapiens
SEQUENCE: 1
MGVKASQTGF VVLVLLQCCS AYKLVCYYTS WSQYREGDGS CFPDALDRFL CTHIIYSFAN    60
ISNDHIDTWE WNDVTLYGML NTLKNRNPNL KTLLSVGGWN FGSQRFSKIA SNTQSRRTFI   120
KSVPPFLRTH GFDGLDLAWL YPGRRDKQHF TTLIKEMKAE FIKEAQPGKK QLLLSAALSA   180
GKVTIDSSYD IAKISQHLDF ISIMTYDFHG AWRGTTGHHS PLFRGQEDAS PDRFSNTDYA   240
VGYMLRLGAP ASKLVMGIPT FGRSFTLASS ETGVGAPISG PGIPGRFTKE AGTLAYYEIC   300
DPFLRGATVHR ILGQQVPYAT KGNQWVGYDD QESVKSKVQY LKDRQLAGAM VWALDLDDFQ   360
GSFCGQDLRF PLTNAIKDAL AAT                                           383

SEQ ID NO: 2              moltype = AA   length = 389
FEATURE                   Location/Qualifiers
source                    1..389
                          mol_type = protein
                          organism = Mus musculus
SEQUENCE: 2
MHTSTEARMG MRAALTGFAV LMLLQSCSAY KLVCYFTSWS QYREGVGSFL PDAIQPFLCT    60
HIIYSFANIS SDNMLSTWEW NDESNYDKLN KLKTRNTNLK TLLSVGGWKF GEKRFSEIAS   120
NTERRTAFVR SVAPFLRSYG FDGLDLAWLY PRLRDKQYFS TLIKELNAEF TKEVQPGREK   180
LLLSAALSAG KVAIDTGYDI AQIAQHLDFI NLMTYDFHGV WRQITGHHSP LFQGQKDTRF   240
DRYSNVNYAV QYMIRLGAQA SKLLMGIPTF GKSFTLASSE NQLGAPISGE GLPGRFTKEA   300
GTLAYYEICD FLKGAEVHRL SNEKVPFATK GNQWVGYEDK ESVKNKVGFL KEKKLAGAMV   360
WALDLDDFQG TCQPKEFFPL TNAIKDALA                                     389

SEQ ID NO: 3              moltype = AA   length = 123
FEATURE                   Location/Qualifiers
source                    1..123
                          mol_type = protein
                          organism = synthetic construct
SEQUENCE: 3
MAEVQLLESG GGLVQPGGSL RLSCAASGFR DSDEDMGWVR QAPGKGLEWV SSISAPGGST    60
YYADSVKGRF TISRDNSKNT LYLQMNSLRA EDTAVYYCAS HYNYGHWFDY WGQGTLVTVS   120
SAA                                                                 123

SEQ ID NO: 4              moltype = AA   length = 123
FEATURE                   Location/Qualifiers
source                    1..123
                          mol_type = protein
                          organism = synthetic construct
SEQUENCE: 4
MAEVQLLESG GGLVQPGGSL RLSCAASGFR DSDEDMGWVR QAPGKGLEWV SSISADSGST    60
YYADSVKGRF TISRDNSKNT LYLQMNSLRA EDTAVYYCAS DYNYWYWFDY WGQGTLVTVS   120
SAA                                                                 123

SEQ ID NO: 5              moltype = AA   length = 10
FEATURE                   Location/Qualifiers
source                    1..10
                          mol_type = protein
                          organism = synthetic construct
SEQUENCE: 5
GFRDSDEDMG                                                           10

SEQ ID NO: 6              moltype = AA   length = 16
FEATURE                   Location/Qualifiers
source                    1..16
                          mol_type = protein
                          organism = synthetic construct
SEQUENCE: 6
ISAPGGSTYY ADSVKG                                                    16

SEQ ID NO: 7              moltype = AA   length = 10
FEATURE                   Location/Qualifiers
source                    1..10
                          mol_type = protein
                          organism = synthetic construct
SEQUENCE: 7
HYNYGHWFDY                                                           10

SEQ ID NO: 8              moltype = AA   length = 10
FEATURE                   Location/Qualifiers
source                    1..10
                          mol_type = protein
                          organism = synthetic construct
```

```
SEQUENCE: 8
GFRDSDEDMG                                                                  10

SEQ ID NO: 9             moltype = AA   length = 16
FEATURE                  Location/Qualifiers
source                   1..16
                         mol_type = protein
                         organism = synthetic construct
SEQUENCE: 9
ISADSGSTYY ADSVKG                                                           16

SEQ ID NO: 10            moltype = AA   length = 10
FEATURE                  Location/Qualifiers
source                   1..10
                         mol_type = protein
                         organism = synthetic construct
SEQUENCE: 10
DYNYWYWFDY                                                                  10

SEQ ID NO: 11            moltype = AA   length = 10
FEATURE                  Location/Qualifiers
source                   1..10
                         mol_type = protein
                         organism = synthetic construct
SEQUENCE: 11
GFRDSDEDMG                                                                  10

SEQ ID NO: 12            moltype = AA   length = 16
FEATURE                  Location/Qualifiers
source                   1..16
                         mol_type = protein
                         organism = synthetic construct
SEQUENCE: 12
ISAXXGSTYY ADSVKG                                                           16

SEQ ID NO: 13            moltype = AA   length = 10
FEATURE                  Location/Qualifiers
source                   1..10
                         mol_type = protein
                         organism = synthetic construct
SEQUENCE: 13
XYNYXXWFDY                                                                  10

SEQ ID NO: 14            moltype = AA   length = 213
FEATURE                  Location/Qualifiers
source                   1..213
                         mol_type = protein
                         organism = synthetic construct
SEQUENCE: 14
DIQMTQSPAS LSASVGETVT ITCGASENIY GALNWYQRKQ GKSPQLLIYG ATTLADGMSS           60
RFSGSGSGRQ YSLKISSLHP DDVATYYCQN VLTTPWTFGG GTKLEIKTVA APSVFIFPPS          120
DEQLKSGTAS VVCLLNNFYP REAKVQWKVD NALQSGNSQE SVTEQDSKDS TYSLSSTLTL          180
SKADYEKHKV YACEVTHQGL SSPVTKSFNR GEC                                       213

SEQ ID NO: 15            moltype = AA   length = 454
FEATURE                  Location/Qualifiers
source                   1..454
                         mol_type = protein
                         organism = synthetic construct
SEQUENCE: 15
EVQLQQSGAE LVKPGASVKL SCTASGFNIK DTYMHWVKQR PEQGLEWIGR IDPANGNTIY           60
ASKFQGKATI TRDTSSNTAY MQLSSLTSGD TAVYYCTRGV YYYGGSFYAM DYWGQGTSVT          120
VSSAASTKGP SVFPLAPSSK STSGGTAALG CLVKDYFPEP VTVSWNSGAL TSGVHTFPAV          180
LQSSGLYSLS SVVTVPSSSL GTQTYICNVN HKPSNTKVDK KVEPKSCDKT HTCPPCPAPE          240
LLGGPSVFLF PPKPKDTLMI SRTPEVTCVV VDVSHEDPEV KFNWYVDGVE VHNAKTKPRE          300
EQYNSTYRVV SVLTVLHQDW LNGKEYKCKV SNKALPAPIE KTISKAKGQP REPQVYTLPP          360
SREEMTKNQV SLTCLVKGFY PSDIAVEWES NGQPENNYKT TPPVLDSDGS FFLYSKLTVD          420
KSRWQQGNVF SCSVMHEALH NHYTQKSLSL SPGK                                     454

SEQ ID NO: 16            moltype = AA   length = 11
FEATURE                  Location/Qualifiers
source                   1..11
                         mol_type = protein
                         organism = synthetic construct
SEQUENCE: 16
GASENIYGAL N                                                                11

SEQ ID NO: 17            moltype = AA   length = 7
FEATURE                  Location/Qualifiers
```

```
source                      1..7
                            mol_type = protein
                            organism = synthetic construct
SEQUENCE: 17
GATTLAD                                                                 7

SEQ ID NO: 18               moltype = AA   length = 9
FEATURE                     Location/Qualifiers
source                      1..9
                            mol_type = protein
                            organism = synthetic construct
SEQUENCE: 18
QNVLTTPWT                                                               9

SEQ ID NO: 19               moltype = AA   length = 7
FEATURE                     Location/Qualifiers
source                      1..7
                            mol_type = protein
                            organism = synthetic construct
SEQUENCE: 19
GFNIKDT                                                                 7

SEQ ID NO: 20               moltype = AA   length = 6
FEATURE                     Location/Qualifiers
source                      1..6
                            mol_type = protein
                            organism = synthetic construct
SEQUENCE: 20
DPANGN                                                                  6

SEQ ID NO: 21               moltype = AA   length = 14
FEATURE                     Location/Qualifiers
source                      1..14
                            mol_type = protein
                            organism = synthetic construct
SEQUENCE: 21
GVYYYGGSFY AMDY                                                        14

SEQ ID NO: 22               moltype = AA   length = 227
FEATURE                     Location/Qualifiers
source                      1..227
                            mol_type = protein
                            organism = synthetic construct
SEQUENCE: 22
DKTHTCPPCP APELLGGPSV FLFPPKPKDT LMISRTPEVT CVVVDVSHED PEVKFNWYVD        60
GVEVHNAKTK PREEQYNSTY RVVSVLTVLH QDWLNGKEYK CKVSNKALPA PIEKTISKAK       120
GQPREPQVYT LPPSREEMTK NQVSLTCLVK GFYPSDIAVE WESNGQPENN YKTTPPVLDS       180
DGSFFLYSKL TVDKSRWQQG NVFSCSVMHE ALHNHYTQKS LSLSPGK                    227

SEQ ID NO: 23               moltype = AA   length = 223
FEATURE                     Location/Qualifiers
source                      1..223
                            mol_type = protein
                            organism = synthetic construct
SEQUENCE: 23
VECPPCPAPP VAGPSVFLFP PKPKDTLMIS RTPEVTCVVV DVSHEDPEVQ FNWYVDGMEV        60
HNAKTKPREE QFNSTFRVVS VLTVVHQDWL NGKEYKCKVS NKGLPAPIEK TISKTKGQPR       120
EPQVYTLPPS REEMTKNQVS LTCLVKGFYP SDIAVEWESN GQPENNYKTT PPMLDSDGSF       180
FLYSKLTVDK SRWQQGNVFS CSVMHEALHN HYTQKSLSLS PGK                        223

SEQ ID NO: 24               moltype = AA   length = 9
FEATURE                     Location/Qualifiers
source                      1..9
                            mol_type = protein
                            organism = synthetic construct
SEQUENCE: 24
FRDSDEDMG                                                               9

SEQ ID NO: 25               moltype = AA   length = 15
FEATURE                     Location/Qualifiers
source                      1..15
                            mol_type = protein
                            organism = synthetic construct
SEQUENCE: 25
SIGDESGSTY YADSV                                                       15

SEQ ID NO: 26               moltype = AA   length = 15
FEATURE                     Location/Qualifiers
source                      1..15
```

```
                         mol_type = protein
                         organism = synthetic construct
SEQUENCE: 26
SINAPDGSTY YADSV                                                      15

SEQ ID NO: 27            moltype = AA  length = 15
FEATURE                  Location/Qualifiers
source                   1..15
                         mol_type = protein
                         organism = synthetic construct
SEQUENCE: 27
SISGSDGSTY YADSV                                                      15

SEQ ID NO: 28            moltype = AA  length = 15
FEATURE                  Location/Qualifiers
source                   1..15
                         mol_type = protein
                         organism = synthetic construct
SEQUENCE: 28
SINNSGGSTY YADSV                                                      15

SEQ ID NO: 29            moltype = AA  length = 15
FEATURE                  Location/Qualifiers
source                   1..15
                         mol_type = protein
                         organism = synthetic construct
SEQUENCE: 29
SISAESGSTY YADSV                                                      15

SEQ ID NO: 30            moltype = AA  length = 15
FEATURE                  Location/Qualifiers
source                   1..15
                         mol_type = protein
                         organism = synthetic construct
SEQUENCE: 30
SINYNSGSTY YADSV                                                      15

SEQ ID NO: 31            moltype = AA  length = 15
FEATURE                  Location/Qualifiers
source                   1..15
                         mol_type = protein
                         organism = synthetic construct
SEQUENCE: 31
SISDEDGSTY YADSV                                                      15

SEQ ID NO: 32            moltype = AA  length = 15
FEATURE                  Location/Qualifiers
source                   1..15
                         mol_type = protein
                         organism = synthetic construct
SEQUENCE: 32
SISGESGSTY YADSV                                                      15

SEQ ID NO: 33            moltype = AA  length = 15
FEATURE                  Location/Qualifiers
source                   1..15
                         mol_type = protein
                         organism = synthetic construct
SEQUENCE: 33
SIQSSDGSTY YADSV                                                      15

SEQ ID NO: 34            moltype = AA  length = 15
FEATURE                  Location/Qualifiers
source                   1..15
                         mol_type = protein
                         organism = synthetic construct
SEQUENCE: 34
SINNESGSTY YADSV                                                      15

SEQ ID NO: 35            moltype = AA  length = 15
FEATURE                  Location/Qualifiers
source                   1..15
                         mol_type = protein
                         organism = synthetic construct
SEQUENCE: 35
SIYAPNGSTY YADSV                                                      15

SEQ ID NO: 36            moltype = AA  length = 15
FEATURE                  Location/Qualifiers
```

```
                           -continued source                 1..15
                       mol_type = protein
                       organism = synthetic construct
SEQUENCE: 36
SIASDSGSTY YADSV                                                    15

SEQ ID NO: 37          moltype = AA   length = 15
FEATURE                Location/Qualifiers
source                 1..15
                       mol_type = protein
                       organism = synthetic construct
SEQUENCE: 37
SIGAGSGSTY YADSV                                                    15

SEQ ID NO: 38          moltype = AA   length = 15
FEATURE                Location/Qualifiers
source                 1..15
                       mol_type = protein
                       organism = synthetic construct
SEQUENCE: 38
SINANDGSTY YADSV                                                    15

SEQ ID NO: 39          moltype = AA   length = 15
FEATURE                Location/Qualifiers
source                 1..15
                       mol_type = protein
                       organism = synthetic construct
SEQUENCE: 39
SIGNYNGSTY YADSV                                                    15

SEQ ID NO: 40          moltype = AA   length = 15
FEATURE                Location/Qualifiers
source                 1..15
                       mol_type = protein
                       organism = synthetic construct
SEQUENCE: 40
SIYGPSGSTY YADSV                                                    15

SEQ ID NO: 41          moltype = AA   length = 15
FEATURE                Location/Qualifiers
source                 1..15
                       mol_type = protein
                       organism = synthetic construct
SEQUENCE: 41
SIDAEDGSTY YADSV                                                    15

SEQ ID NO: 42          moltype = AA   length = 10
FEATURE                Location/Qualifiers
source                 1..10
                       mol_type = protein
                       organism = synthetic construct
SEQUENCE: 42
TSDSYWSFDY                                                          10

SEQ ID NO: 43          moltype = AA   length = 10
FEATURE                Location/Qualifiers
source                 1..10
                       mol_type = protein
                       organism = synthetic construct
SEQUENCE: 43
QWDDGYAFDY                                                          10

SEQ ID NO: 44          moltype = AA   length = 10
FEATURE                Location/Qualifiers
source                 1..10
                       mol_type = protein
                       organism = synthetic construct
SEQUENCE: 44
TDYLRSSFDY                                                          10

SEQ ID NO: 45          moltype = AA   length = 10
FEATURE                Location/Qualifiers
source                 1..10
                       mol_type = protein
                       organism = synthetic construct
SEQUENCE: 45
TYDWNYSFDY                                                          10

SEQ ID NO: 46          moltype = AA   length = 10
```

```
FEATURE                 Location/Qualifiers
source                  1..10
                        mol_type = protein
                        organism = synthetic construct
SEQUENCE: 46
QYGAYHDFDY                                                                      10

SEQ ID NO: 47           moltype = AA  length = 10
FEATURE                 Location/Qualifiers
source                  1..10
                        mol_type = protein
                        organism = synthetic construct
SEQUENCE: 47
TPNLNSSFDY                                                                      10

SEQ ID NO: 48           moltype = AA  length = 10
FEATURE                 Location/Qualifiers
source                  1..10
                        mol_type = protein
                        organism = synthetic construct
SEQUENCE: 48
SGDWWYGFDY                                                                      10

SEQ ID NO: 49           moltype = AA  length = 10
FEATURE                 Location/Qualifiers
source                  1..10
                        mol_type = protein
                        organism = synthetic construct
SEQUENCE: 49
VDPLDTYFDY                                                                      10

SEQ ID NO: 50           moltype = AA  length = 10
FEATURE                 Location/Qualifiers
source                  1..10
                        mol_type = protein
                        organism = synthetic construct
SEQUENCE: 50
SSQNGYVFDY                                                                      10

SEQ ID NO: 51           moltype = AA  length = 10
FEATURE                 Location/Qualifiers
source                  1..10
                        mol_type = protein
                        organism = synthetic construct
SEQUENCE: 51
TSYYGFDFDY                                                                      10

SEQ ID NO: 52           moltype = AA  length = 8
FEATURE                 Location/Qualifiers
source                  1..8
                        mol_type = protein
                        organism = synthetic construct
SEQUENCE: 52
NTYDAFDY                                                                         8

SEQ ID NO: 53           moltype = AA  length = 10
FEATURE                 Location/Qualifiers
source                  1..10
                        mol_type = protein
                        organism = synthetic construct
SEQUENCE: 53
SGYAGTVFDY                                                                      10

SEQ ID NO: 54           moltype = AA  length = 10
FEATURE                 Location/Qualifiers
source                  1..10
                        mol_type = protein
                        organism = synthetic construct
SEQUENCE: 54
STDARWQFDY                                                                      10

SEQ ID NO: 55           moltype = AA  length = 10
FEATURE                 Location/Qualifiers
source                  1..10
                        mol_type = protein
                        organism = synthetic construct
SEQUENCE: 55
QYDDEFAFDY                                                                      10
```

```
SEQ ID NO: 56          moltype = AA   length = 10
FEATURE                Location/Qualifiers
source                 1..10
                       mol_type = protein
                       organism = synthetic construct
SEQUENCE: 56
VSDSGFSFDY                                                                10

SEQ ID NO: 57          moltype = AA   length = 10
FEATURE                Location/Qualifiers
source                 1..10
                       mol_type = protein
                       organism = synthetic construct
SEQUENCE: 57
SDWDGYSFDY                                                                10

SEQ ID NO: 58          moltype = AA   length = 10
FEATURE                Location/Qualifiers
source                 1..10
                       mol_type = protein
                       organism = synthetic construct
SEQUENCE: 58
QDGAYYTFDY                                                                10

SEQ ID NO: 59          moltype = AA   length = 11
FEATURE                Location/Qualifiers
source                 1..11
                       mol_type = protein
                       organism = synthetic construct
SEQUENCE: 59
SISTSDGSTY Y                                                              11

SEQ ID NO: 60          moltype = AA   length = 10
FEATURE                Location/Qualifiers
source                 1..10
                       mol_type = protein
                       organism = synthetic construct
SEQUENCE: 60
QYDTGYSFDY                                                                10

SEQ ID NO: 61          moltype = AA   length = 365
FEATURE                Location/Qualifiers
source                 1..365
                       mol_type = protein
                       organism = synthetic construct
SEQUENCE: 61
STQSPSVFPL TRCCKNIPSN ATSVTLGCLA TGYFPEPVMV TWDTGSLNGT TMTLPATTLT          60
LSGHYATISL LTVSGAWAKQ MFTCRVAHTP SSTDWVDNKT FSVCSRDFTP PTVKILQSSC         120
DGGGHFPPTI QLLCLVSGYT PGTINITWLE DGQVMDVDLS TASTTQEGEL ASTQSELTLS         180
QKHWLSDRTY TCQVTYQGHT FEDSTKKCAD SNPRGVSAYL SRPSPFDLFI RKSPTITCLV         240
VDLAPSKGTV NLTWSRASGK PVNHSTRKEE KQRNGTLTVT STLPVGTRDW IEGETYQCRV         300
THPHLPRALM RSTTKTSGPR AAPEVYAFAT PEWPGSRDKR TLACLIQNFM PEDISVQWLH         360
NEVQL                                                                    365

SEQ ID NO: 62          moltype = AA   length = 229
FEATURE                Location/Qualifiers
source                 1..229
                       mol_type = protein
                       organism = synthetic construct
SEQUENCE: 62
RSPPLKECPP CAAPDLLGGP SVFIFPPPKIK DVLMISLSPM VTCVVVDVSE DDPDVQISWF         60
VNNVEVHTAQ TQTHREDYNS TLRVVSALPI QHQDWMSGKE FKCKVNNRAL PSPIEKTISK        120
PRGPVRAPQV YVLPPPAEEM TKKEFSLTCM ITGFLPAEIA VDWTSNGRTE QNYKNTATVL        180
DSDGSYFMYS KLRVQKSTWE RGSLFACSVV HEGLHNHLTT KTISRSLGK                    229
```

ANTIBODIES AGAINST YKL-40 AND USES THEREOF

SEQUENCE LISTING

The instant application contains a Sequence Listing which has been submitted electronically as a file in XML format and is hereby incorporated by reference in its entirety. Said XML format file, created on Apr. 28, 2023, is named Sequence_list_BIOY0002PA.xml and is 57,066 bytes in size.

TECHNICAL FIELD

The present invention relates to YKL-40 antibodies capable of binding to human and murine YKL-40. These antibodies are useful for multiple purposes, including for detection of YKL-40, for treatment of cancers, or delaying the onset of cancers or for treatment of other diseases associated with aberrant YKL-40 expression, in particular YKL-40 overexpression. Such diseases include e.g. inflammatory diseases.

BACKGROUND

YKL-40 is a 40 kDa heparin- and chitin-binding glycoprotein also known as human cartilage glycoprotein 39 (HC gp-39), 38-kDa heparin-binding glycoprotein or chitinase-3-like protein 1 (CHI3L1). The abbreviation YKL-40 is based on the one letter code for the first three N-terminal amino acids, tyrosine (Y), lysine (K) and leucine (L) and the apparent molecular weight of YKL-40.

YKL-40 was first identified as a protein secreted in large amounts by a human osteosarcoma cell line MG63 in vitro. Later studies have found that YKL-40 is secreted in vitro by a variety of cells and seems especially involved in activation of the innate immune system and in cell processes in relation to extracellular matrix remodeling.

The crystallographic structure of human YKL-40 has been described and the protein contains two globular domains: a big core domain which consists of a $(\beta/\alpha)_8$ domain structure with a triose-phosphatase isomerase (TIM) barrel fold and a small $\alpha/\beta$ domain, composed of five antiparallel $\beta$-strands and one $\alpha$-helix, inserted in the loop between strand $\beta7$ and helix $\alpha7$. This confers the active site of YKL-40 a groove-like character.

The folded protein contains two potential hyaluronan binding sites predicted by in silico methods. Binding of short and long oligosaccharides to human YKL-40 are also possible.

YKL-40 possesses several biological activities. It has been shown that human YKL-40 can act as a growth factor for cells of connective tissue, such as chondrocytes and synovial cells. YKL-40 also promotes the growths of fibroblasts in a fashion like insulin-like growth factor 1 (IGF-1). It has also been demonstrated that YKL-40 can act as a chemoattractant for endothelial cells and stimulates migration of these cells comparable to stimulation by basic fibroblast growth factor. YKL-40 is also found to modulate vascular endothelial cell morphology by promoting formation of branching tubules. A strong expression of YKL-40 mRNA in human liver has been shown to be associated with the presence of fibrosis. Immunohistochemical studies of liver biopsies have shown YKL-40 protein expression in areas of the liver with fibrosis, whereas no expression was observed in hepatocytes. Patients with non-malignant diseases characterized by inflammation and fibrosis such as active rheumatoid arthritis, severe bacterial infections, active inflammatory bowel disease, and liver fibrosis have elevated serum levels of YKL-40.

YKL-40 is expressed and secreted by several types of human malignancies. Furthermore, YKL-40 is found to be secreted in vitro by the osteosarcoma cell line MG63, glioblastoma cells and myeloid leukemia cell lines. Several studies have reported an elevated level of YKL-40 protein in serum of cancer patients.

Thus, YKL-40 activity is found to be associated with cell growth, survival, differentiation, apoptosis, angiogenesis, extracellular matrix remodeling, development of metastasis, development of liver or tissue fibrosis, development of rheumatoid arthritis and/or development of inflammation.

SUMMARY

There is an unmet need of additional YKL-40 antibodies, and in particularly for YKL-40 antibodies useful in treatment of cancer. Furthermore, there is a need for additional YKL-40 antibodies, which are capable of binding to both murine and human YKL-40.

The invention provides antibodies useful for administration to human beings because said antibodies contains either mainly human sequences (e.g. B3 of SEQ ID NO: 3 or B10 of SEQ ID NO: 4) or they are chimeric antibodies comprising human sequences (e.g. H7 comprising SEQ ID NO: 14 and SEQ ID NO: 15).

The invention is further defined in the claims attached hereto.

Figure 8:
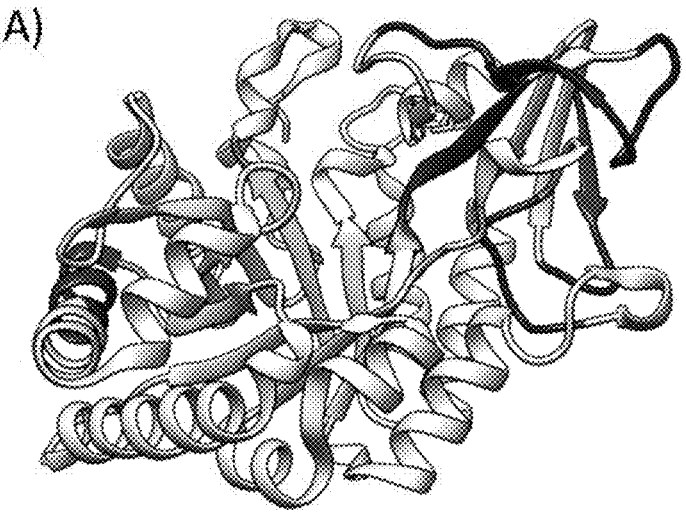
FIG. 8: Epitope mapping of H7 antibody
Figure 8:
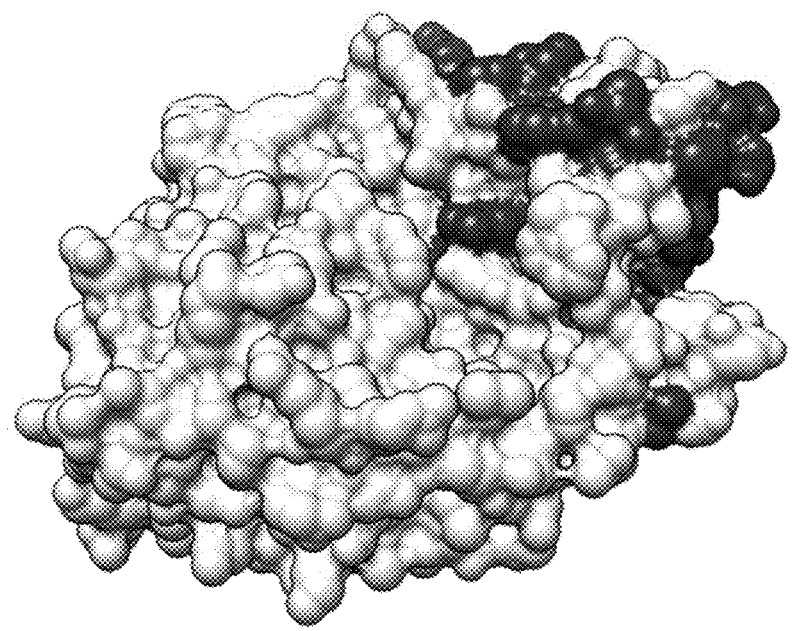

Epitope mapping of H7 (SEQ ID NO: 14 and SEQ ID NO: 15) antibody was performed using linear peptide arrays as described in Geysen et al. Peptides were synthesized as mimics. Peptides were either 15-mers with 14 amino acid overlap, an additional set of 10-mers, looped 8-mers, helical-stabilized peptides of 19 amino acid length or continuous beta-turn mimics of 20 amino acid length. Epitopes of H7 comprising or positioned within a sequence selected from amino acids 123-130 or 218-224 or 259-265 or 269-286 or 303-315 of SEQ ID NO: 1. The epitope of H7 is thus believed to comprise or be positioned within the aforementioned sequences. The position of the sequences are shown in FIGS. 8A and 8B in black.

Figure 9:
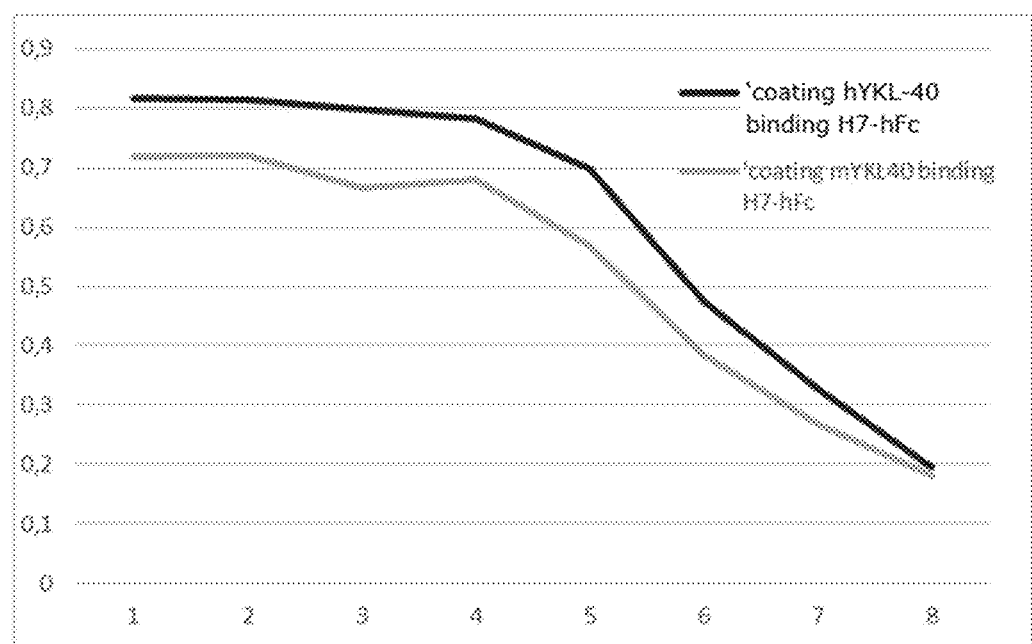

FIG. 9 shows, that H7 (SEQ ID NO: 14 and 15) binds to human YKL-40 and to a lesser extent to murine YKL-40 in a dose dependent manner in a ELISA assay. Different concentrations of H7 antibody was tested as indicated in Example 10.

DETAILED DESCRIPTION

Definitions

Figure 1:
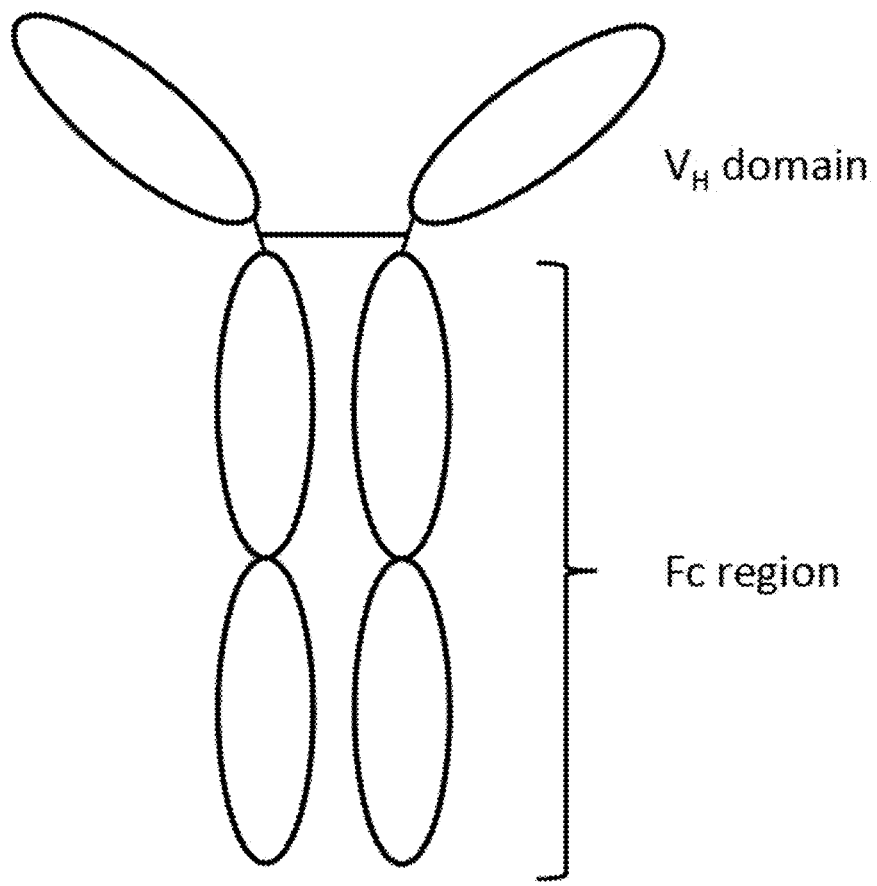
FIG. 1: shows three common antibody formats. Different fragments from the immunoglobulin are often used in recombinant formats, especially the variable domains of the heavy chain $V_H$ have been used repeatedly. A) a variable domain of the heavy chain ($V_H$) linked to a constant region of the heavy chain (Fc region). B) a variable domain of the heavy chain ($V_H$). Domain antibodies may consists of only a $V_H$ C) Example of a chimeric antibody. There are three human/murine chimeric complementary-determining regions (CDRs) (CDR1, 2 and 3) arranged non-consecutively on the amino acid sequence of a variable domain of an antigen receptor.
Figure 1:
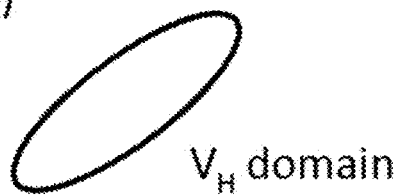
Figure 1:
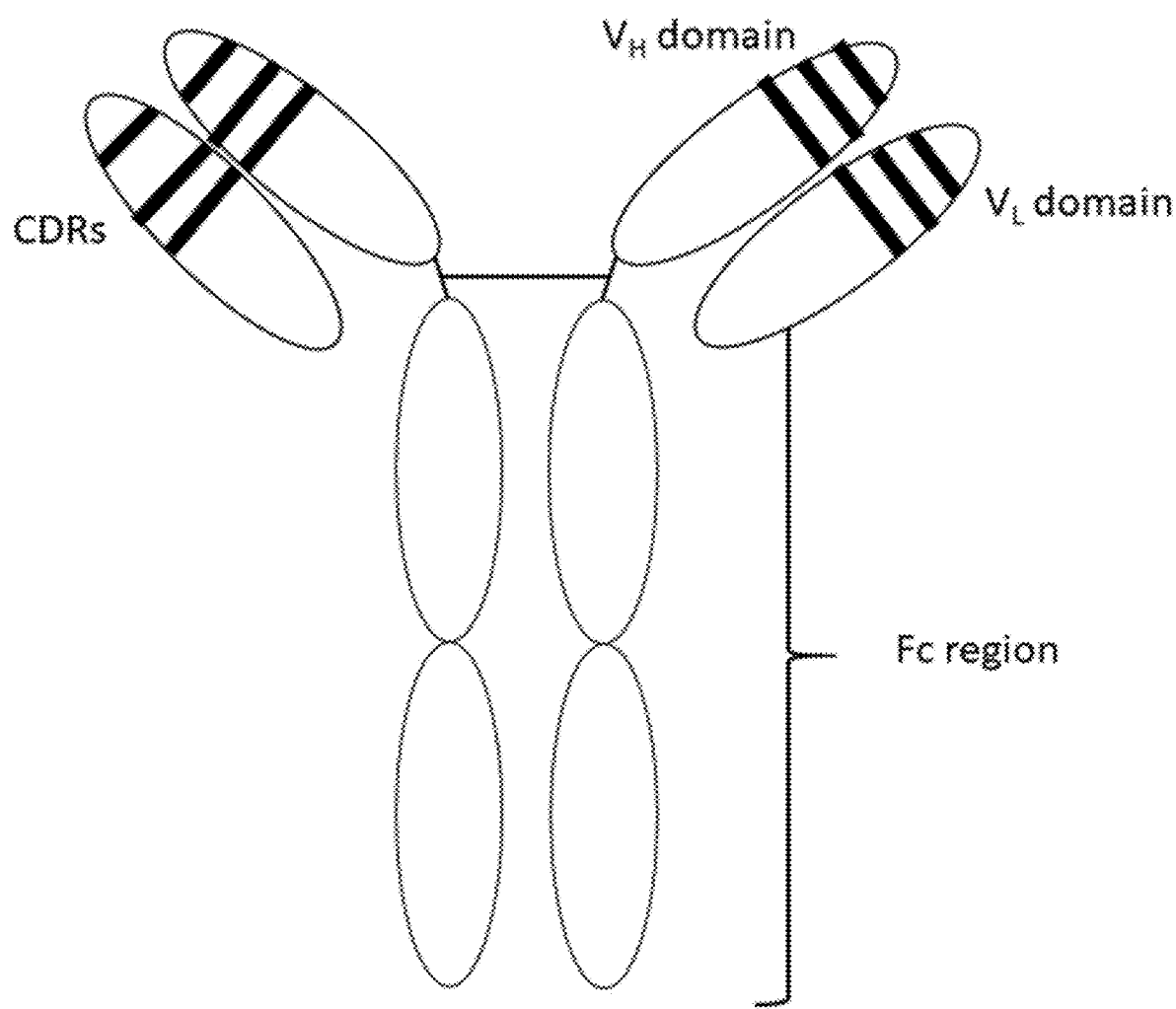

The term "antibody" as used herein refers to a polypeptide, which is capable of binding a specific antigen via an epitope on the antigen. An antibody comprises at least one antigen binding site, wherein said antigen binding site comprises 3 Complementarity-determining regions (CDRs), such as a CRD1, CDR2 and CDR3. The antigen binding site may in particular be a variable region, such as a heavy chain or light chain variable region. Whereas most antibodies comprises a heavy chain comprising an antigen binding site and a light chain comprising another an antigen binding site, some antibodies are single-domain antibodies comprising only one antigen binding site. Single-domain antibodies consisting of heavy chains only are e.g. found in camelids. Typically, the antigen binding site of an antibody is positioned within an antibody variable region. Suitable variable regions include, but are not necessarily limited to Fv fragments, heavy chain variable regions and light chain variable regions. Variable regions may be connected and thus they may form or be part of e.g. single chain Fv (scFv) and disulphide-bonded Fv, Fab-like fragments (e.g. Fab fragments, Fab' fragments and F(ab)2 fragments), and domain antibodies (dAbs, including single and dual formats [i.e. dAb-linker-dAb]). Variable regions may be linked to an Fc region. Thus, an antibody heavy chain usually consists of a heavy chain variable region and a heavy chain Fc region. Similarly, an antibody light chain usually consists of a light chain variable region and a light chain Fc region. Single-domain antibodies typically consists of variable region comprising 3 CDRs and a constant region of a heavy chain in one polypeptide. Various antibody chains may be linked to each other, e.g. by disulphide bonds. Thus, a heavy chain and a light chain may be linked to each other. Furthermore, a heavy chain and a light chain pair, may be linked to another (frequently identical) heavy chain/light chain pair. The heavy chain of a single domain antibody may also be linked to another (frequently identical) heavy chain, e.g. by disulphide bonds, thereby forming an antibody made up of two constant domains of the heavy chains and two variable domains of the heavy chain, wherein said Fc regions are joined by disulphide bonds (see FIG. 1).

"Cellular cytotoxicity therapy" involves the transfer of immune cells (e.g. T-cells, NK-cells, dendritic cells, granulocytes and/or macrophages) with anti-malignant tumour activity into cancer patients. It is a treatment approach that usually involves the identification of cells with anti-malignant tumour activity, the expansion of these cells to large numbers and their infusion into the cancer-bearing host.

An "effective amount" or "therapeutically effective amount" of a compound is that amount of compound which is sufficient to provide a beneficial effect to the subject to which the compound is administered. The phrase "therapeutically effective amount," as used herein, may refer to an amount of antibody that is sufficient or effective to treat (delay or prevent the onset of, prevent the progression of, inhibit, decrease or reverse) a clinical condition, e.g. an inflammatory condition or cancer.

The term "Fc region" is abbreviated form of "fragment crystallisable region". "Fc region" as used herein refers to the C-terminal constant region of an immune globulin heavy chain. The Fc region may be a "native" or "wild-type" sequence Fc region, or a variant Fc region. The Fc region may be any constant region of IgM, IgD, IgG IgA and IgE. A native Fc region is normally homodimeric and comprises two polypeptide chains. In respect of preparing YKL-40 antibodies a variable domain, such as $V_H$, may be linked to a "single-chain" Fc region (scFc region), which may later form a dimeric antibody comprising two $V_H$ domains and two scFc regions.

The term "Immunotherapeutic agent" refers to an agent capable of inducing, enhancing and/or suppressing an immune response. In particular, an immunotherapeutic agent is an agent useful in the treatment of disease.

The term "immunotherapy" refers to treatment of disease by activating, augmenting and/or suppressing the natural, humoral and/or adaptive immune system. Immunotherapy may be cell-based therapy such as cellular cytotoxicity therapy or non-cell based. Immunotherapy may be antibody therapy with antibodies from either the natural or the adaptive immune system. Immunotherapy may also be therapy with immunomodulators such as cytokines, interleukins and/or chemokines. Immunotherapy may also be treatment aimed at modulating or enhancing interactions with immunomodulators and classical anti-neoplastic agents. Examples of useful types of immunotherapies are described in the FIG. 3 of the review article by Melero et al. Evolving synergistic combinations of targeted immunotherapies to combat cancer. Nature Reviews 2015, 15:457472. Other useful types of immunotherapies are described below.

The term "naturally occurring antibody" refers to an antibody comprising two identical heavy chains and two identical light chains linked to another, wherein the heavy and light chains of the antibody have been made and paired by the immune system of a multi-cellular organism. Spleen, lymph nodes and bone marrow are examples of tissues that produce natural antibodies. For example, the antibodies produced by the antibody producing cells isolated from a first animal immunized with an antigen are natural antibodies. Naturally occurring antibody are heterotetrameric glycoproteins capable of recognising and binding an antigen and comprising two identical heavy (H) chains and two identical light (L) chains inter-connected by disulfide bonds. Each heavy chain comprises a heavy chain variable region (abbreviated herein as $V_H$) and a heavy chain constant region (abbreviated herein as CH). Each light chain comprises a light chain variable region (abbreviated herein as $V_L$) and a light chain constant region (abbreviated herein as CL). The $V_H$ and $V_L$ regions can be further subdivided into regions of hypervariability, termed complementarity determining regions (CDRs), interspersed with regions that are more conserved, termed framework regions (FRs). Antibodies may comprise several identical heterotetramers.

The term "monoclonal antibody" as used herein refers to an antibody obtained from a population of substantially homogeneous antibodies, i.e., the individual antibodies making up the population are identical except for possible minor differences. Said minor differences may be the result of post-translational modification and/or degradation or they may be caused by naturally occurring mutations that may be present in minor amounts.

The terms "solid neoplasm", "solid malignant tumour", and "malignant tumour" are herein used interchangeably. The term "cancer" refers to a disease, which may be characterised by the presence of at least one "solid neoplasm", "solid malignant tumour" or "malignant tumour".

The term "variable" in the context of variable domain of antibodies, refers to the fact that certain portions of the variable domains differ extensively in sequence among antibodies. The variable domains are for binding and determine the specificity of each particular antibody for its specifically recognized antigen. However, the variability is not evenly distributed through the variable domains of antibodies. It is concentrated in three segments called complementarity determining regions (CDRs) also known as hypervariable regions both in the light chain and the heavy chain variable domains.

The term "treatment" refers to any kind of treatment, including preventive, ameliorating/palliative or curative treatment. Treatment may thus result in the prevention, decrease and/or amelioration/palliation of causes and/or symptoms of malignant tumours and cancers. Moreover, the treatment can also stop or slow down disease progression, e.g. it may stop or slow down cancer formation, development, or growth.

YKL-40 Antibody

A YKL-40 antibody may be any antibody specifically binding YKL-40. For example, the YKL-antibody of the present invention may be any YKL-40 antibody, wherein said YKL-40 antibody comprises a variable region as defined herein below in the section "Variable region". Thus, the present invention provides antibodies capable of binding to YKL-40, and preferably capable of binding human and murine YKL-40. In particular, said antibodies are capable of binding to an amino acid sequence of SEQ ID NO:1 and of SEQ ID NO:2.

In some embodiments, the YKL-40 antibody comprises a variable region comprising a CDR1, CDR2 and CDR3, wherein,
CDR1 comprises or consists of an amino acid sequence of SEQ ID NO:5;
CDR2 comprises or consists of an amino acid sequence of SEQ ID NO: 6; and
CDR3 comprises or consists of an amino acid sequence of SEQ ID NO: 7. In particular, the YKL-40 antibody may be a single domain antibody comprising a variable region comprising aforementioned CDRs. The antibody may also be a bi- or multispecific antibody made up of several single domain antibodies one of which contains a variable region comprising aforementioned CDRs.

In some embodiments, the YKL-40 antibody comprises a variable region comprising a CDR1, CDR2 and CDR3, wherein,
CDR1 comprises or consists of an amino acid sequence of SEQ ID NO: 8;
CDR2 comprises or consists of an amino acid sequence of SEQ ID NO: 9; and
CDR3 comprises or consists of an amino acid sequence of SEQ ID NO: 10. In particular, the YKL-40 antibody may be a single domain antibody comprising a variable region comprising aforementioned CDRs. The antibody may also be a bi- or multispecific antibody made up of several single domain antibodies one of which contains a variable region comprising aforementioned CDRs.

In some embodiments, the YKL-40 antibody comprises two variable regions each comprising a CDR1, CDR2 and CDR3, wherein,
CDR1 of the light chain comprises or consists of an amino acid sequence of SEQ ID NO: 16;
CDR2 of the light chain comprises or consists of an amino acid sequence of SEQ ID NO: 17;
CDR3 of the light chain comprises or consists of an amino acid sequence of SEQ ID NO: 18;
CDR1 of the heavy chain comprises or consists of an amino acid sequence of SEQ ID NO: 19;
CDR2 of the heavy chain comprises or consists of an amino acid sequence of SEQ ID NO: 20; and
CDR3 of the light chain comprises or consists of an amino acid sequence of SEQ ID NO: 21.

In some embodiments, the YKL-40 antibody comprises at least one variable region comprising or consisting of SEQ ID NO: 3. In particular, the YKL-40 antibody may be a single domain antibody comprising a variable region comprising or consisting of SEQ ID NO: 3. The antibody may also be a bi- or multispecific antibody made up of several single domain antibodies one of which contains a variable region comprising or consisting of SEQ ID NO: 3.

In some embodiments, the YKL-40 antibody comprises at least one variable region comprising or consisting of SEQ ID NO: 4. In particular, the YKL-40 antibody may be a single domain antibody comprising a variable region comprising or consisting of SEQ ID NO: 4. The antibody may also be a bi- or multispecific antibody made up of several single domain antibodies one of which contains a variable region comprising or consisting of SEQ ID NO: 4.

In some embodiments, the YKL-40 antibody comprises at least one variable region of the light chain comprising or consisting of an amino acid sequence of SEQ ID NO: 14 and at least one variable region of the heavy chain comprising or consisting of an amino acid sequence of SEQ ID NO: 15.

In some embodiments, the YKL-40 antibody comprises a variable region comprising a CDR1 comprising or consisting of an amino acid sequence selected from the group consisting of SEQ ID NO: 5 and SEQ ID NO: 8.

In some embodiments, the YKL-40 antibody comprises variable regions comprising a CDR1 of the light chain comprising or consisting of an amino acid sequence of SEQ ID NO: 16 and a CDR1 of the heavy chain comprising or consisting of an amino acid sequence of SEQ ID NO: 19.

In some embodiments, the YKL-40 antibody comprises a light chain variable region comprising a CDR2 comprising or consisting of an amino acid sequence selected from the group consisting of SEQ ID NO: 6 and SEQ ID NO: 9.

In some embodiments, the YKL-40 antibody comprises variable regions comprising a CDR2 of the light chain comprising or consisting of an amino acid sequence of SEQ ID NO: 17 and a CDR2 of the heavy chain comprising or consisting of an amino acid sequence of SEQ ID NO: 20.

In some embodiments, the YKL-40 antibody comprises a light chain variable region comprising a CDR3 comprising or consisting of an amino acid sequence selected from the group consisting of SEQ ID NO: 7 or SEQ ID NO 10.

In some embodiments, the YKL-40 antibody comprises variable regions comprising a CDR3 of the light chain comprising or consisting of an amino acid sequence of SEQ ID NO: 18 and a CDR3 of the heavy chain comprising or consisting of an amino acid sequence of SEQ ID NO: 21.

In some embodiments, the antibody comprises or consists of a variable region comprising or consisting of an amino acid sequence selected from the group consisting of SEQ ID NO: 3 or SEQ ID NO:4.

The YKL-40 antibody of the invention comprising any of the aforementioned variable region may further comprise constant regions. In embodiments, of the invention where the antibody is a single domain antibody, the antibody typically comprises only one of the aforementioned variable regions, e.g. a variable region comprising the CDRs of B3 or B10 fused to one constant region, e.g. an Fc region as described below. In embodiments of the invention, where the antibody comprises two variable regions, each variable region may be fused to a constant region, e.g. to Fc regions. Thus, the YKL-40 antibody may comprise a light chain variable region and a heavy chain variable region comprising the CDRs of H7, each variable region being fused to constant regions, such as Fc regions.

In some embodiments the antibody of the invention is a bi- or multispecific antibody. A bispecific antibody comprises two different antigen binding sites, e.g. different variable regions, specifically binding different epitopes. Preferably, said bi- or multispecific antibody binds to different epitopes on YKL-40. In other words, the bi- or multispecific antibody comprises two different variable regions each binding to YKL-40. Similarly, a multispecific antibody comprises several different antigen binding sites, e.g. different variable regions, specifically binding different epitopes. The antibodies of the invention may thus comprise two or more different variable regions, wherein each variable region may be fused to a constant region, e.g. to Fc regions. Bi- or multispecific antibodies may also be IgA comprising two (or 4) or IgM comprising five (or 10) different variable regions having different epitope specificities. Bi-specific antibodies may be prepared based on any of the YKL-40 antibodies described herein, e.g. using any of the methods described in Wang, Q. et al., 2019.

In one embodiment, the YKL-40 antibody may be a bi-specific antibody comprising or consisting of two different single domain antibodies each capable of specifically binding YKL-40. Each of the single domain antibodies may comprise a variable region specifically binding YKL-40 fused to a constant region, e.g. an Fc region. The skilled person is aware of how to prepare a bi-specific antibody based on two single domain antibodies. This may for example be done by fusing the variable region of the single domain antibodies to different Fc regions comprising mutations allowing for binding between the different Fc regions, e.g. using the knobs and holes strategy (Wang, Q. et al., 2019). For example, one single domain antibody may comprise the heavy chain mutations S354C and T366W, whereas the other single domain antibody may comprise the heavy chain mutations Y349C, T366S, and L368A.

In one embodiment, the YKL-40 antibody may comprise one or more variable regions comprising the CDRS of B3, i.e. CDRs of SEQ ID NOs: 5, 6 and 7 and one or more variable regions comprising the CDRS of B10, i.e. CDRs of SEQ ID NOs: 8, 9 and 10. Each of said variable regions may be attached to a constant region, e.g. an Fc region, and may made into a bi-specific format as described above.

In one embodiment, the YKL-40 antibody may comprise one or more variable regions comprising or consisting of the variable region of B3, i.e. SEQ ID NO: 3 and one or more variable regions comprising or consisting of the variable region of B10, i.e. SEQ ID NO:4. Each of said variable regions may be attached to a constant region, e.g. an Fc region, and may made into a bi-specific format as described above.

In one embodiment, the YKL-40 antibody may comprise one or more variable regions comprising the CDRs of B3, i.e. CDRs of SEQ ID NO: 5-7 and one or more variable regions made up of a $V_L$ and $V_H$, wherein the $V_L$ comprises the CDRs of the light chain variable region of H7, i.e. CDRs of SEQ ID NO: 16-18, and the $V_H$ comprises the CDRs of the heavy chain variable region of H7, i.e. CDRs of SEQ ID NO: 19-21.

In one embodiment, the YKL-40 antibody may comprise one or more variable regions comprising the CDRs of B10, i.e. the CDRs of SEQ ID NO: 8-10 and one or more variable regions made up of a $V_L$ and $V_H$, wherein the $V_L$ comprises the CDRs of the light chain variable region of H7, i.e. CDRs of SEQ ID NO: 16-18, and the $V_H$ comprises the CDRs of the heavy chain variable region of H7, i.e. CDRs of SEQ ID NO: 19-21.

In, one embodiment the YKL-40 antibody may comprise one or more variable regions comprising the CDRs of B3 of SEQ ID NO: 5-7, one or more variable regions comprising the CDRs of B10 of SEQ ID NO: 8-10 and one or more variable regions made up of a $V_L$ and $V_H$, wherein the $V_L$ comprises the CDRs of the light chain variable region of H7, i.e. CDRs of SEQ ID NO: 16-18, and the $V_H$ comprises the CDRs of the heavy chain variable region of H7, i.e. CDRs of SEQ ID NO: 19-21.

In some embodiments, the composition comprises antibodies binding to YKL-40, with the proviso that the antibodies do not comprise any of the following combinations of CDRs:

| Combination no: | CDR1 | CDR2 | CDR3 |
| --- | --- | --- | --- |
| 1 | SEQ ID NO: 24 | SEQ ID NO: 25 | SEQ ID NO: 42 |
| 2 | SEQ ID NO: 24 | SEQ ID NO: 26 | SEQ ID NO: 43 |
| 3 | SEQ ID NO: 24 | SEQ ID NO: 27 | SEQ ID NO: 44 |
| 4 | SEQ ID NO: 24 | SEQ ID NO: 28 | SEQ ID NO: 45 |
| 5 | SEQ ID NO: 24 | SEQ ID NO: 29 | SEQ ID NO: 46 |

-continued

| Combination no: | CDR1 | CDR2 | CDR3 |
|---|---|---|---|
| 6 | SEQ ID NO: 24 | SEQ ID NO: 30 | SEQ ID NO: 47 |
| 7 | SEQ ID NO: 24 | SEQ ID NO: 31 | SEQ ID NO: 48 |
| 8 | SEQ ID NO: 24 | SEQ ID NO: 32 | SEQ ID NO: 49 |
| 9 | SEQ ID NO: 24 | SEQ ID NO: 33 | SEQ ID NO: 50 |
| 10 | SEQ ID NO: 24 | SEQ ID NO: 34 | SEQ ID NO: 51 |
| 11 | SEQ ID NO: 24 | SEQ ID NO: 35 | SEQ ID NO: 52 |
| 12 | SEQ ID NO: 24 | SEQ ID NO: 36 | SEQ ID NO: 53 |
| 13 | SEQ ID NO: 24 | SEQ ID NO: 37 | SEQ ID NO: 54 |
| 14 | SEQ ID NO: 24 | SEQ ID NO: 38 | SEQ ID NO: 55 |
| 15 | SEQ ID NO: 24 | SEQ ID NO: 39 | SEQ ID NO: 56 |
| 16 | SEQ ID NO: 24 | SEQ ID NO: 40 | SEQ ID NO: 57 |
| 17 | SEQ ID NO: 24 | SEQ ID NO: 41 | SEQ ID NO: 58 |
| 18 | SEQ ID NO: 24 | SEQ ID NO: 59 | SEQ ID NO: 60 |

This is in particular the case, when the composition only comprises one antibody specifically binding YKL-40.

In some embodiments, the two YKL-40 antibodies are administered in a ratio of 1:1, such as 1:2, such as 1:3, such as 1:4, such as 1:5, such as 1:10, such as 1:100.

In some embodiments, the two YKL-40 antibodies are administered sequentially or simultaneously, preferably simultaneously.

In some embodiments, the two YKL-40 antibodies are selected from a group consisting of antibodies binding to the same epitope as B3 (SEQ ID NO: 3), binding to the same epitope as B10 (SEQ ID NO: 4) and binding to the same epitope as H7 (SEQ ID NO: 14 and SEQ ID NO: 15).

In some embodiments, the two YKL-40 antibodies is one antibody binding to the same epitope as B3 (SEQ ID NO: 3) and one antibody binding to the same epitope as B10 (SEQ ID NO: 4). Said antibody binding the same epitope as B3, may in particular be an antibody comprising the same CDRs as B3 (i.e. SEQ ID NO: 5, 6 and 7), for example an antibody comprising the variable region of B3 (i.e. SEQ ID NO:3). Said antibody binding the same epitope as B10, may in particular be an antibody comprising the same CDRs as B10 (i.e. SEQ ID NO: 8, SEQ ID NO:9 and SEQ ID NO: 10), for example an antibody comprising the variable region of B10 (i.e. SEQ ID NO:4).

YKL-40 is an extracellular matrix protein, specifically a secretory glycoprotein, which belongs to the mammalian chitinase like family. YKL-40 has been shown to bind collagen, heparin, hyaluronan and chitin. It is mainly produced by macrophages, neutrophils and cancer cells. YKL-40 plasma levels are increased in cancer patients compared to healthy subjects.

An antibody that is contemplated for use in the present invention can be in any of a variety of forms, including a whole immunoglobulin, an antibody fragment such as Fv, Fab, Fab' or F(ab')$_2$ fragments, a single chain antibody which comprises the variable regions of a heavy and a light chain linked together or single domain antibodies.

In one embodiment, the antibody of the invention is a single domain antibody. Single domain antibodies usually comprises a variable region optionally linked to an Fc region. Thus, the antibody of the invention may consist of a variable region. Alternatively, the antibody may consist of a variable region linked to an Fc region. The variable region may for example consist of either of a $V_H$ domain or a $V_L$ domain, or another similar variable region. In particular, the single domain antibody may comprise a variable region and an Fc region derived from a human antibody, e.g. from a human heavy chain.

In one embodiment, the antibody comprises a variable region comprising a CDR1, CDR2 and CDR3 as defined herein below. The variable region may be selected from the group consisting of a $V_H$ domain, $V_L$ domain or scFv. It is preferred that the variable region comprises or consists of a $V_H$ domain.

In another embodiment, the variable region of said antibody is linked to an Fc region, optionally by a linker. Thus, the antibody according to the invention may comprise or consist of a $V_H$ domain linked to an Fc region, optionally via a linker. Hereby forming a single chain antibody, which comprises the CDRs of a variable domain of the heavy chain and the constant region of the heavy chain in one polypeptide.

In yet another embodiment, the antibody may comprise or consist of two single domain antibodies. Thus, the antibody according to the invention may consist or comprise of two $V_H$ domains, wherein each $V_H$ domain is linked to an Fc region, wherein said Fc regions are linked to each other by bonds, such as by disulphide bonds.

The antibodies according to the present invention are in general monoclonal antibodies.

In one embodiment, the antibody of the invention is a chimeric antibody. Chimeric antibodies retains CDRs from its original species incorporated into the antibody from another species, such as humans. Other chimeric antibodies retain the variable regions from its original species fused to constant regions of another species, such a humans. Advantages of chimeric antibodies are a reduced immunogenicity in humans compared to murine antibodies and a cheaper production compared to what is required for generating a fully humanized antibody. In the United States, several different chimeric antibodies have already been approved for clinical use by the Food and Drug Administration (FDA).

The antibody can be a multispecific antibody (e.g. bispecific antibody) formed from at least two different antibodies, and/or antibody fragments so long as they exhibit binding to YKL-40.

In one embodiment, the antibody is a human antibody or an antibody based on human scaffold. For example, the antibody may be a human single domain antibody. Human single domain antibodies may in particular comprise or consists of a human $V_H$ domain optionally linked to a human Fc region. The antibody may also be a single domain antibody based on human sequences, wherein diversity has been generated synthetically. Such antibodies are useful in the treatment of human beings. The antibody may also be a humanised antibody comprising CDR regions (and possibly a few other residues) transferred from another species having the desired specificity, affinity, and capacity. Humanised antibodies may also comprise synthetic CDR regions, e.g. from a synthetic antibody library.

The generation of antibodies may be achieved by any standard methods in the art for producing antibodies.

For generation and/or selection of YKL-40 antibodies, YKL-40 protein or a fragment thereof is used. Preferably, the method comprises use of a natural YKL-40 protein, such as a secreted and optionally purified YKL-40 protein. Alternatively, a recombinant YKL-40 protein or fragment thereof may also be employed. In particular, YKL-40 secreted from MG63 cells may be employed. Medium in which MG63 cells have been cultivated may be used in crude form or YKL-40 may be partly or fully purified from such medium. Alternatively, YKL-40 secreted from the mouse myeloma cell line NS0 may be employed. Medium in which the mouse myeloma cell line NS0 have been cultivated may be used in crude form or YKL-40 may be partly or fully purified from such medium. Recombinant antibodies may be isolated from libraries of genes encoding fragments of antibodies, e.g. using aforementioned YKL-40 protein or fragments thereof for selection. The fragments of antibodies can for example be any of the aforementioned antibody fragments, such as Fab, Fv fragments, single chain fragment of heavy and light chain variable domains or single domain antibodies, such as polypeptides comprising or consisting of $V_H$ or $V_L$ domains. The libraries of genes may be obtained from natural sources, as in the case of naïve or immunised libraries, or they may be created by synthetic means. Isolation of specific antibodies from the libraries can be mediated by panning of phage displayed antibody libraries on specific antigens or complex mixtures, such as described in Mandrup et al., 2013. Libraries may be obtained by panning of phage displayed antibody libraries on a specific antigen from several species in several rounds. The phage displayed antibody libraries may be screened by successive selection on YKL-40 or a fragment thereof from humans followed by panning the phage displayed antibody libraries on YKL-40 from mice or a fragment of murine YKL-40 corresponding to the fragment from human YKL-40. These pannings may be performed in either order. Alternatively, methods such as yeast display, bacterial display, ribosome display, etc. can be applied in the selection of monoclonal recombinant antibodies.

The antibody may be a human single domain antibody or a single domain antibody based on human sequences, wherein diversity has been artificially generated. Several different libraries of useful human single domain antibodies are available. Thus, the antibody may be selected by screening any library of human single domain antibodies with YKL-40 protein or fragment(s) thereof. Such libraries include, but are not limited to human domain antibody libraries using the HEL4 scaffold, as well as such libraries, which have been counter-selected for aggregation, wherein the CDR regions of the resulting clones have been sub-cloned and used for generating a new library with diversity in all three CDR regions as described in Christ et al., 2007. Other useful libraries include Pansri et al., 2009, Rothe et al., 2008, Fellouse et al., 2007, Hust et al., 2004, Silacci et al., 2005 and Brockmann et al., 2011.

A preferred library to be used is the domain antibody library with constant CDR1 and restricted randomizations at 4 and 7 positions in the CDR2 and CDR3 described in Mandrup et al., 2013. This library is based on the aggregation resistant human HEL4 domain antibody scaffold with the inclusion of a hydrophilic mutation at position 29. The diversity of this library is designed to reflect the amino acid composition of CDR regions from known functional human antibody clones.

Once a variable domain capable of binding YKL-40 has been selected, said variable domain may be used as YKL-40 antibody per se, but it may also be fused to other domains, e.g. an Fc domain.

This may e.g. be achieved by using an expression vector allowing fusion of single chain Fv antibodies or single domains, such as single $V_H$ domains to Fc regions of immunoglobulins. This method is useful for the generation of multi-species antibodies and enables fusion of single chain Fv antibodies or single $V_H$ domains with human, mouse or rabbit Fc and can be applied to natural monoclonal antibodies cloned as single chain Fv antibodies. The expression vector can be for example a pFuse expression system, such as pFUSE-hFc1 or pFUSE-mFc1 as described by Moutel et al., 2009. Thus, an antibody comprising or consisting of a $V_H$ domain linked to an Fc region can be generated. Such antibodies can then dimerize and form an antibody of two $V_H$ domain which are each linked to an Fc region, wherein the two Fc regions are linked by disulphide bonds. Preferably, said Fc region is a human Fc region. Non-limiting examples of useful Fc regions include the Fc region of SEQ ID NO: 22 or SEQ ID NO: 23. In other embodiments the Fc region is a murine Fc, such as the Fc region of SEQ ID NO:62.

In one embodiment, the antibody is a chimeric antibody wherein the variable part is fused with an Fc region of a different species.

This means, that a portion of the heavy and/or light chain of the antibody is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Morrison et al. 1984).

The invention contemplates human and humanized forms of non-human (e.g. murine) antibodies. Such humanized antibodies are chimeric immunoglobulins, immunoglobulin chains or fragments thereof (such as Fv, Fab, Fab', F(ab')2 or other antigen-binding subsequences of antibodies) that contain a minimal sequence derived from non-human immunoglobulin, such as the epitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Alternatively, humanized antibodies are human immunoglobulins (recipient antibody) in which the entire variable region has been replaced by a variable region from a nonhuman species. Humanized antibodies containing a minimal sequence of antibodies of the invention, such as a sequence recognising the epitopes described herein, is a preferred embodiment of the invention. In particular, in some embodiments, the invention relates to humanized forms of mouse anti-human YKL-40 monoclonal antibody H7 (SEQ ID NO: 14 and SEQ ID NO: 15). Alternatively, humanized antibodies are human immunoglobulins (recipient antibody) in which the entire variable region has been replaced by a variable region from a nonhuman species.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., 1986).

In some embodiments, the YKL-40 antibody is binding one or more epitopes comprising or positioned within a sequence selected from amino acids 123-130 or 218-224 or 259-265 or 269-286 or 303-315 of SEQ ID NO: 1.

In some embodiments, the YKL-40 antibody is binding one or more epitopes comprising or positioned within a sequence selected from amino acids 46-58 or 76-127 or 192-203 or 213-225 or 234-247 or 250-269 or 274-286 or 294-314 or 359-373 of SEQ ID NO: 1.

In some embodiments, the YKL-40 antibody is binding one or more epitopes comprising or positioned within a sequence selected from amino acids 76-92 or 99-131 or 134-158 or 161-182 or 212-225 or 240-263 or 275-286 or 303-324 or 326-348 of SEQ ID NO: 1.

In some embodiments, the YKL-40 antibody is binding one or more epitopes comprising or positioned within a sequence selected from amino acids 123-127 or 218-224 or 259-263 or 275-286 or 303-314 of SEQ ID NO: 1.

In some embodiments, the YKL-40 antibody is binding one or more epitopes comprising or positioned within a sequence selected from amino acids 123-127 or 218-224 or 259-263 or 275-286 or 304-314 of SEQ ID NO: 1.

In some embodiments, the YKL-40 antibody is binding one or more epitopes comprising or positioned within a sequence selected from amino acids 218-224 of SEQ ID NO: 1.

In some embodiments, the YKL-40 antibody is binding one or more epitopes comprising or positioned within a sequence selected from amino acids 218-224 or 269-273 of SEQ ID NO: 1.

In some embodiments, the YKL-40 antibody is binding one or more epitopes comprising or positioned within a sequence selected from amino acids 46-58 or 76-92 or 192-201 or 216-225 or 234-247 or 274-286 or 294-300 or 359-373 of SEQ ID NO: 1.

In some embodiments, the YKL-40 antibody is binding one or more epitopes comprising or positioned within a sequence selected from amino acids 76-92 or 145-158 or 161-182 or 216-225 or 240-250 or 314-324 or 326-348 of SEQ ID NO: 1.

Variable Region

The antibody according to the present invention comprises a variable region. The variable region can be in any form, comprising a CDR1, CDR2 and CDR3. Thus, the variable region may be a single domain consisting of either $V_H$ or $V_L$ domains, scFv, Fab, Fab' or F(ab')$_2$ fragments. In some embodiments, the variable region is a $V_H$ domain, for example a human $V_H$ domain or a $V_H$ domain based on human sequences, such as a $V_H$ domain as described by Mandrup et al., 2013. In other embodiments, the variable region is a $V_H$ domain, for example, a chimeric $V_H$ domain based on human and murine sequences, such as a $V_H$ domain as described by Jones et al., 1986.

The variable domains are for binding and determine the specificity of each particular antibody for its particular antigen. However, the variable region is not normally evenly distributed thought the variable region of antibodies. It is concentrated in CDRs also known as hyper variable regions. The more highly conserved portions of variable domains are called the framework (FR). The variable domains of native heavy and light chains each comprise four FR regions connected by three CDRs. It is preferred that the FR regions are human FR regions, or at least highly identical to human FR regions.

In one embodiment, the antibody binds to YKL-40, wherein binding to YKL-40 inhibits or prevents binding of YKL-40 to another molecule. Binding of the antibody to YKL-40 can result in activation, stimulation or inhibition of YKL-40. Thus, binding of the antibody to YKL-40 may results in activation, stimulation or inhibition of YKL-40.

In one embodiment, the antibody is an inhibitor of YKL-40. Thus, the YKL-40 antibody may result in inhibition of at least one function of YKL-40.

In one embodiment, the antibody binds to an epitope on human and murine YKL-40. Thereby, the antibody binds partially or completely to an epitope within residues 1-383 of YKL-40, such as residues 1-50 of YKL-40, such as residues 50-100 of YKL-40, such as residues 100-150 of YKL-40, such as residues 150-200 of YKL-40, such as residues 200-250 of YKL-40, such as residues 250-300 of YKL-40, such as residues 300-350 of YKL-40, such as residues 350-383 of YKL-40.

In one embodiment, the YKL-40 antibody binds preferably to the same epitope as an YKL-40 antibody comprising the variable region of SEQ ID NO:3.

In one embodiment, the YKL-40 antibody binds preferably to the same epitope as an YKL-40 antibody comprising the variable region of SEQ ID NO:4.

In one embodiment, the YKL-40 antibody binds preferably to the same epitope as an YKL-40 antibody comprising a light chain variable region of SEQ ID NO:14 and a heavy chain variable regions of SEQ ID NO: 15.

Constant Region or Fc Region

The antibody according to the present invention comprises a variable region, which may be linked to any constant region, for example any Fc region.

Traditionally, antibodies have been grouped based on the constant domain of their heavy chains, i.e. Fc region, into five classes IgM, IgD, IgG IgA and IgE. Which can be further divided into subclasses (isotypes), e.g. IgG-1, IgG-2, IgG-3 and IgG-4; IgA-1 and IgA-2.

In some embodiments, the heavy chain has the amino acid sequence of a human IgA heavy chain. In some embodiments, the heavy chain has the amino acid sequence of a human IgM heavy chain. In some embodiments, the heavy chain has the amino acid sequence of a human IgE heavy chain. In some embodiments, the heavy chain has the amino acid sequence of a human IgG heavy chain. In some embodiments, the heavy chain has the amino acid sequence of a human IgD heavy chain.

In some embodiments, the heavy chain has the amino acid sequence of a mouse IgA heavy chain. In some embodiments, the heavy chain has the amino acid sequence of a mouse IgM heavy chain. In some embodiments, the heavy chain has the amino acid sequence of a mouse IgE heavy chain. In some embodiments, the heavy chain has the amino acid sequence of a mouse IgG heavy chain. In some embodiments, the heavy chain has the amino acid sequence of a mouse IgD heavy chain.

In some embodiments, the antibody according to the present invention comprises a variable region which may be linked to any constant region of another antibody. The constant region may be identical to a "native" or "wild-type" Fc region, or a variant Fc region with at least one alteration of an amino acid.

In one embodiment, the Fc region has the amino acid sequence of a human IgE Fc region, e.g. the sequence provided herein as SEQ ID NO: 61. A suitable Fc region is described in Moutel et al., 2009.

As mentioned herein above, the antibody may be a bispecific antibody, which e.g. may be designed as described in Wang et al., 2019. In such cases the variable regions may be linked to slightly different Fc regions as described above.

Method of Treatment

The present invention also concerns a method of treating diseases associated with aberrant YKL-40 expression. Such method comprises administering an YKL-40 antibody as described herein above, to a subject in need thereof.

Said treatment may be a curative treatment, but it may also be preventive treatment to delay onset of said disease, or it may be treatment to delay disease progression. Further, it may be ameliorating treatment or treatment of symptoms of said disease.

The disease may for example be cancer, such as any of the cancers described herein below.

In one embodiment, the invention relates to a method of treating cancer, the method comprising administering an YKL-40 antibody according to the invention to a subject in need thereof. In a preferred embodiment, the invention relates to a method of treating cancer, the method comprising administering a composition of at least one YKL-40 antibody, such as two YKL-40 antibodies, such as three YKL-40 antibodies, such as five YKL-40 antibodies according to the invention to a subject in need thereof.

In some embodiments, the invention relates to a method of treating cancer, the method comprising administering two different YKL-40 antibodies. Preferably, said two antibodies are selected from a group consisting of antibodies binding to the same epitope as B3 (SEQ ID NO: 3), binding to the same epitope as B10 (SEQ ID NO: 4) and binding to the same epitope as H7 (SEQ ID NO: 14 and SEQ ID NO: 15).

In some embodiments, the invention relates to a method of treating cancer, the method comprising administering two different YKL-40 antibodies. Preferably, one YKL-40 antibody binds to the same epitope as B3 (SEQ ID NO: 3) and the other YKL-40 antibody binds to the same epitope as B10 (SEQ ID NO: 4). In preferred embodiments, one YKL-40 antibody comprises the same CDRs as B3 (i.e. SEQ ID NO: 5, 6 and 7) and the other YKL-40 antibody comprises the same CDRs as B10 (i.e. SEQ ID NO: 8, SEQ ID NO:9 and SEQ ID NO: 10). Even more preferably, one antibody comprises the variable region of B3 (i.e. SEQ ID NO: 3) and the other antibody comprises the variable region of B10 (i.e. SEQ ID NO:4).

In another embodiment, the invention relates to a method for delaying onset of cancer, the method comprising administering a therapeutically effective amount of an YKL-40 antibody according to the invention, to a subject in need thereof.

The disease to be treated with the YKL-40 antibody according to the invention may also be an inflammatory disease. For example the disease may be an inflammatory disease on the lungs, such as asthma and/or rheumatic diseases. In some embodiments, the rheumatic disease to be treated with the YKL-40 antibody according to the invention is arthritis, such as osteoarthritis.

The subject to be treated with the antibody of the invention may in particular be a human being, because the antibodies of the invention preferably are based on human antibody sequences.

The invention also comprises diagnostic and theranostic methods useful to determine whether a subject is susceptible to a method of treatment. The term "theranostics" generally refers to therapy-specific diagnostics, which is the use of diagnostic testing to determine the efficacy of a given treatment regime for that disease, and/or monitor the patient response to therapy. Theranostic tests can be used to predict and assess response in individual patients, and can be used to improve efficacy by selecting treatments effective for a given patient.

Anti-Cancer Agent

Additional anti-cancer agents may be administered together with or subsequent or prior to a YKL-40 antibody or a combination of YKL-40 antibodies.

Thus, the anti-cancer agent may be any anti-cancer agent. The invention is not limited to a particular type of anti-cancer agent, because increasing permeability facilitates penetration of all compounds into solid malignant tumour. Thus, the anti-cancer agent may be small molecules, biological macro-molecules, cells, hormones or mixtures thereof.

In one embodiment, the anti-cancer agent is selected from the group consisting of a chemotherapeutic agent, an immunotherapeutic agent, a biologic agent, checkpoint inhibitors, anti-cancer antibodies, a cytostatic small molecule and statins.

In one embodiment the anti-cancer agent is a small molecule. Small molecules according to the invention are preferably an organic compound with a molecular weight of <900 daltons. In particular, said small molecule may be a chemotherapeutic agent.

The chemotherapeutic agent may be any chemotherapeutic agent. For example, the chemotherapeutic agent may be selected from the group consisting of antimetabolites, anti-malignant tumour antibiotics, topoisomerase inhibitors, mitotic inhibitors, kinase inhibitors, vinca alkaloids, anthracyclines, aromatase inhibitors, mTor inhibitors and retinoids.

In one embodiment, the anti-malignant tumour antibiotic is daunomycin or doxorubicin. In another embodiment, the chemotherapeutic agent is cisplatin.

In one embodiment, the anti-cancer agent is a small molecule inhibitor for example a small molecule kinase inhibitor, a small molecule proteasome inhibitor and a small molecule inhibitor targeting the apoptosis.

In one embodiment, the chemotherapeutic agent is selected form the group Fluorouracil (5-FU), Irinotecan, Oxaliplatin, Capecitabine, Gemcitabine, Nab-paclitaxel and cisplatin.

In one embodiment, the immunotherapeutic agent is a cell-based immunotherapy. In a preferred embodiment, the immunotherapeutic agent is T-cell therapy. The T cell therapy can involve adoptive cell transfer where T cells are extracted, cultivated and transfused in the subject. Genetically engineered T cells and genetically and non-genetically modified NK-cell can also be used as T or NK-cell cell therapy. Harvested T cells are infected with a retrovirus that contains a copy of a T cell receptor (TCR) gene that is specialised to recognise malignant tumour antigens. T cells are expanded and transfused in the subject. T-cells for adoptive Immunotherapy of cancer may for example be any of the ones described in Karahan et al., 2022. The immunotherapeutic agent can also be an autologous enhancement therapy where the subjects own or allogenic immune cells such as natural killer cells, cytotoxic T cells, mesenchymal stem cells or other immune cells are expanded in vitro and then transfused into the said subject.

Immune checkpoints are inhibitory regulators that act as inhibitors on the immune response. Targeting these checkpoints prevents cancers/malignant tumours from evading the immune system. In one embodiment, the checkpoint inhibitors are selected from the group consisting of inhibitors of PDL-1, PD1, CTLA4, and/or LAG3.

In one embodiment, it is preferred that the anti-cancer agent is not an immune checkpoint inhibitor. In one embodiment, it is preferred that the anti-cancer agent is not an immunotherapeutic agent.

In one embodiment, the anti-cancer agent is an anti-cancer antibody. Multiple antibodies are known to be useful in the treatment of cancer. The anti-cancer agent may be any such antibody. For example, the anti-cancer agent may be selected from the group consisting of Trastuzumab, Bevacizumab, Cetuximab, Panitumumab, Ipilimumab, Rituximab, Alemtuzumab and Ofatumumab.

In one embodiment, the anti-cancer agent is a cytostatic small molecule. The cytostatic small molecule may for example be a tyrosine-kinase inhibitor. It can also be a small molecule kinase inhibitor, a small molecule proteasome inhibitor and a small molecule inhibitor targeting apoptosis. It can also be a serine/threonine-kinase inhibitor such as Temsirolimus, Everolimus, Vemurafenib, Trametinib and Dabrafenib. In another embodiment, the cytostatic small molecule is selected from the group consisting of Imatinib, Gefitinib, Erlotinib, Sorafenib, Sunitinib, Dasatinib, Lapatinib, Nilotinib, Bortezomib, tamoxifen, janus kinas inhibitors, ALK inhibitors, Bcl-2 inhibitors, PARP inhibitors, e. g. olaparib, APatinib, Braf inhibitors, MEK inhibitors, CDK inhibitors, Hsp90 inhibitors, and salinomycin.

In one embodiment, the statins are selected from the group consisting of avastatin, lovastatin, rosuvastatin, simvastatin, fluvastatin, pitavastatin, and pravastatin.

In one embodiment, the anti-cancer agent is an antibody-drug conjugate (ADC). For example the ADC may bind a malignant tumour-associated target antigen and deliver a cytotoxic agent to the malignant tumour. The ADC is composed of a monoclonal antibody, a linker and a cytotoxin. For example, the ADC is Trastuzumab emtansine which is an antibody-drug conjugate consisting of the monoclonal antibody trastuzumab linked to the cytotoxic agent emtansine (DM1).

In another embodiment, the anti-cancer agent is coupled to ADCC thereby utilizing the response of innate immune cells to provide anti-malignant tumour cytotoxicity triggered by the interaction of the Fc portion of an antibody with the Fc receptor on the immune cell.

In another embodiment the anti-cancer agent is associated with a nano-particle or a liposome. Thus the anticancer agent may e.g. be protein-bound paclitaxel, also known as nanoparticle albumin-bound paclitaxel or nab-paclitaxel. In this formulation, paclitaxel is bonded to albumin as a delivery vehicle. In another embodiment, the anti-cancer agent may be for example Abraxane® or a pegylated (polyethylene glycol coated) liposome-encapsulated form of doxorubicin, as e.g. Caelyx®. In yet another embodiment, the anti-cancer agent may be for example liposomal irinotecan. These are liposomal constructs that have been engineered to encapsulate chemotherapy thereby preventing premature metabolism, improving distribution and minimizing toxicity (i.e. Onyvide®).

In one embodiment, the anti-cancer agent is selected from the therapeutic groups listed in table 1. In another embodiment, the anti-cancer agent is selected from the drug examples listed in table 1.

Figure 3:
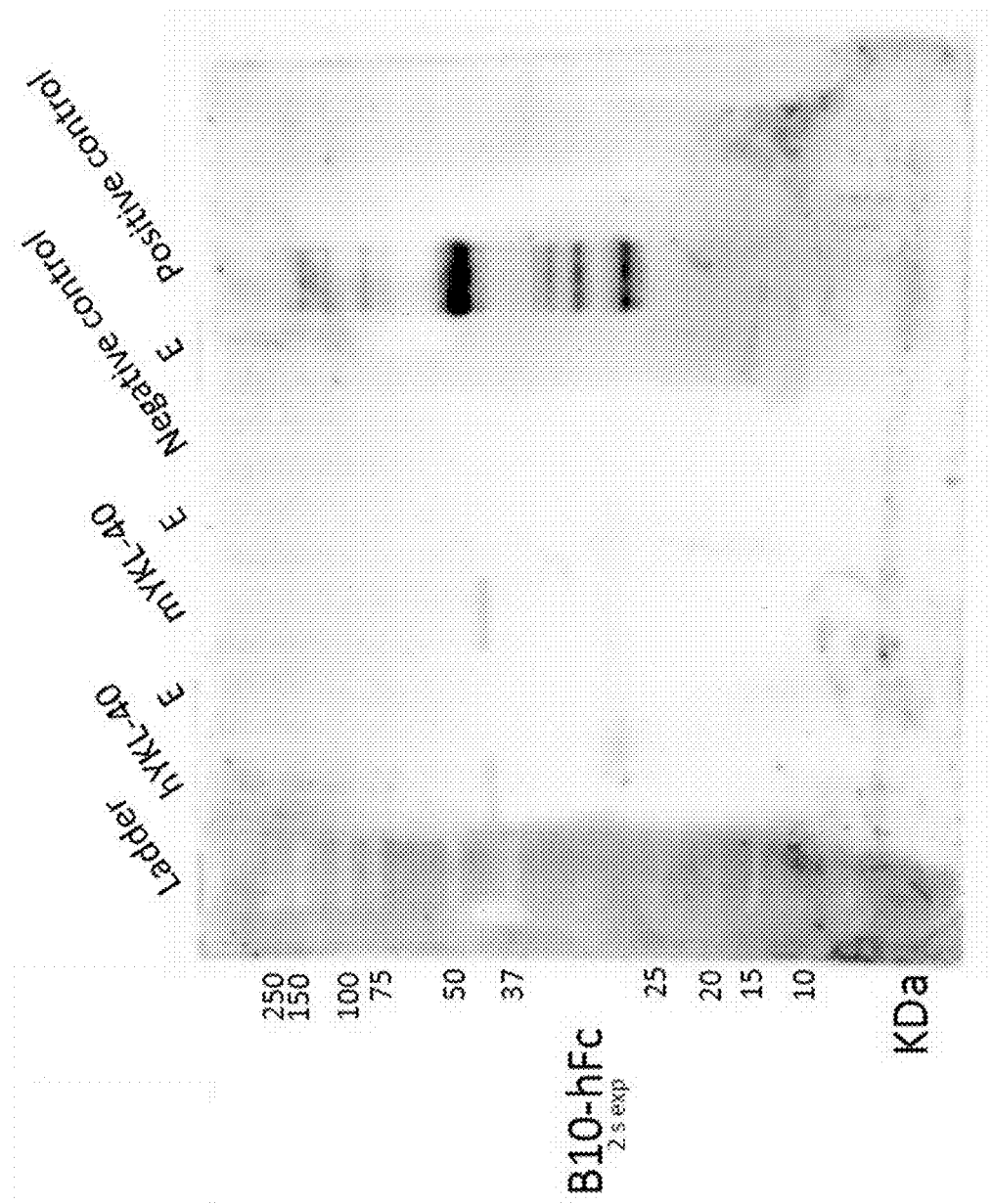
FIG. 3 shows, that B10 (SEQ ID NO: 4)-hFc binds to both human and mouse YKL-40. For the western blot 0.5 µg hYKL-40 or mYKL-40 were loaded onto a 4-20% SureP-AGE, Bis-TRIS gel. The gel was run at 120V for 70 min and afterwards the samples were transferred to a nitrocellulose membrane using iBlot system. The membrane was incubated with 1 µg/ml primary antibody B10 (SEQ ID NO: 4)-hFc.

In one embodiment, the anti-cancer agent is immunotherapy, such as any of the immunotherapies described in Melero et al. 2015 (see above), such as any of the therapies shown in FIG. 3 of Melero et al. 2015 (see above). In one embodiment, the anti-cancer agent is immunotherapy. For example, immunotherapy can be immuno-stimulatory monoclonal antibodies, neutralizing immune inhibitors, cytokines, adoptive T cell therapy, cancer vaccines and microbial adjuvants.

In one embodiment, the immunostimulatory monoclonal antibodies are selected from the group consisting of antibodies to CTLA4, PD1, PDL1, LAG3, TIM3, CD137, OX40, GITR and CD40. In another embodiment, the neutralizing immune inhibitors are selected from the group consisting of TGFbeta, IL-10 and IDO1. In yet another embodiment, the cytokines are selected from the group consisting of IFN alpha, IL-2 and IL-12. In one embodiment, the microbial adjuvants are selected from the group consisting of TLR agonists, alpha-GalCer and STING activators. However, as noted above in some embodiments it is preferred that the anti-cancer agent is not an immune checkpoint inhibitor.

The immunotherapy may also be a cell based immunotherapy, for example the immunotherapy may be based on T-cells, NK-cells, dendritic cells, mesenchymal stem cells or modified cells such as CAR-T Cells, CAR-NK cells or T-cells used in conjunction with the BiTE (Bi-specific T cell engager).

In one embodiment, the anti-cancer agent is selected from the group consisting of radiotherapy, chemotherapy and signal transduction inhibitors. In another embodiment, the chemotherapy is selected from the group consisting of alkylating agents, platinum, antimetabolites, tubulin-inhibitors, antibiotics with anti-cancer effect and cytostatic molecules. In another embodiment, the signal transduction inhibitors are selected from the group consisting of protein kinase inhibitors, signal inhibitors not affecting the protein kinases, the monoclonal antibodies in cancer therapy, hormones and hormone antagonists, cytokines, antibodies towards immunological checkpoints, oncolytic virus, immunological adjuvants, T-cell or dendritic cell therapy and cancer vaccines.

The anti-cancer agent may be a radioactive substance, e.g. substances used in iodine therapy of thyroid cancer. Other radioactive anti-cancer agents may be any of the Radiopharmaceuticals us described in Benfante et al., 2023 and Chakraborty et al., 2023.

TABLE 1

Synergistic therapeutic groups, chemical groups and drug examples

| Therapeutic group | Chemical group | Drug example |
| --- | --- | --- |
| Radiotherapy | Co-stimulatory drugs enhancing the effect of radiotherapy | |
| Chemotherapy | | |
| Alkylating agents | | |
| | Derivatives of mustargen | Klormetin |
| | | Cyclofosfamide |
| | | Clorambucil |
| | | Melphalan |
| | | Ifosphamid |
| | | Trofosfamid |
| | | Bendamustin |
| | | Estramustin |

TABLE 1-continued

Synergistic therapeutic groups, chemical groups and drug examples

| Therapeutic group | Chemical group | Drug example |
|---|---|---|
| | Ethylenephosphoramides | Thiotepa |
| | Alkylsulphonates | Busulfan |
| | | Treosulfan |
| | Nitrosurea compounds | Carmustin |
| | | Lomustin |
| | | Semustin |
| | | Streptozocin |
| | | Chlorozotocin |
| | Triazenes | Dacarbazin |
| | (non-classical alkylating drugs) | Procarbazin |
| | | Altretamin |
| | | Temozolomid |
| Platinum | | |
| | | Cisplatin |
| | | Carboplatin |
| | | Oxaliplatin |
| | | Nedaplatin |
| | | Lobaplatin |
| | | Hetaplatin |
| | | Satraplatin |
| | | Picoplatin |
| Antimetabolites | | |
| | Folic acid | Metotrexat |
| | | Ralitrexed |
| | | Pemetrexed |
| | Purin antagonists | Mercaptopurin |
| | | Cladribin |
| | | Fludarabin |
| | | Chlorfarabin |
| | Pyrimidin antagonists | 5-Fluorouracil |
| | | Capecitabin |
| | | S-1: Tegafur, Gimeracil and oteracil |
| | | Cytarabin |
| | | Gemcitabin |
| Tubulin-inhibitors | | |
| | Vinca-alkaloids | Vinblastin |
| | | Vincristin |
| | | Vindesin |
| | | Vinorelbin |
| | | Vinflunine |
| | | Eribulin |
| | Taxanes | Paclitaxel |
| | | Docetaxel |
| | | Carbazitaxel |
| | | Nanoparticle albumin-bound paclitaxel or nab-paclitaxel, |
| Antibiotics with anticancer effect | | |
| | Anthracyclines | Doxorubicin |
| | | Daunorubicin |
| | | Epirubicin |
| | | Idarubicin |
| | | Mitoksantron |
| | | (Novatrone) |
| | | Polyethylene glycol coated liposome-encapsulated form of doxorubicin |
| | Other antibiotics | Dactinomycin |
| | | Bleomycin |
| | | Mitomycin |
| Other cytostatic molecules | | |
| | Camptothecins | Irinotecan |
| | | Topotecan |
| | | Liposomal Irinotecan |
| | Epipodofyllotoxins | Etoposid |
| | | Etoposidfosfat |
| | | Teniposid |
| | Other Cytostatic | Amsacrin |
| | | Hydroxurea |
| | | Mitotan |
| | | Asparaginase/Crisantaspase |
| | | Tretinoin |

TABLE 1-continued

Synergistic therapeutic groups, chemical groups and drug examples

| Therapeutic group | Chemical group | Drug example |
| --- | --- | --- |
| | | Mitoguazon |
| | | Olaparib |
| Signal transduction inhibitors | | |
| Protein kinase inhibitors | Inhibitors of the ErbB (HER) family in human cancer comprising the epidermal growth factor receptor EGFR (ErbB1), HER2 (ErbB2), HER3 (ErbB3) HER4 (ErbB4) | Erlotinib |
| | | Gefitinib |
| | | Afatinib |
| | | Patatinib |
| | | Imatinib |
| | BCR-ABL, KIT, PDGFR, SRC, VEGFR | Imatinib |
| | | Nilotinib |
| | | Dasatinib |
| | | Bosutinib |
| | | Panotinib |
| | VEGFR1, 2, 3, PDGFR beta, KIT, RET, Raf, PDGFRalfa, beta, FLT3 | Sorafenib |
| | | Sunitinib |
| | VEGFR1, 2, 3, PDGFR, PDGFR alfa, PDGFR beta, FGFR1, 2, KIT, RET, RAF, FLT3 | Pazopanib |
| | | Aksitinib |
| | | Vandetanib |
| | | Regorafenib |
| | ALK and or MET inhibitors | Crizotinib |
| | | Ceritinib |
| | BRAF inhibitors | Vemurafenib |
| | | Dabrafenib |
| | mTOR inhibitors | Temsirolimus |
| | | Everolimus |
| | JAK1-3 inhibitors, TYK2 | Ruxolitinib |
| | Brutons tyrosine kinases | Ibrutinib |
| | More than 500 of the genes in the genome codes for protein kinases and about 100 for tyrosine kinases. | |
| | TK = tyrosine kinase | |
| | RTK = receptor tyrosine kinase | |
| | EGF = epidermal growth factor | |
| | HER-family = human EGFR receptor family | |
| | ABL = Abelson-kinase | |
| | KIT = receptor for stem cell factor | |
| | VEGFR = vascular endothelial growth factor | |
| | ALK = anaplastic lymphoma kinase | |
| | mTOR mammalian target for Rapamycin | |
| | JAK = Janus kinases | |
| Signal inhibitors not affecting the protein kinases | Proteasome | Bortezomid |
| | | Ixazomib |
| | | Carfilzomib |
| | Unknown | Anagrelid |
| | VEGF | Aflibercept |
| Monoclonal antibodies in cancer therapy | | |
| | Unconjugated | Rituximab |
| | | Ofatumumab |
| | | Alemtuzumab |
| | | Trastuzumab |
| | | Pertuzumab |
| | | Cetuximab |
| | | Panitumumab |
| | | Bevacizumab |
| | | Catumaxomab |
| | Immune modulating T-cell activating agents | Ipilimumab |
| | | Nivolumab |
| | | Pembrolizumab |
| | | Many more in development |
| | Immuno-conjugates | Y90-marked ibritumomab Tiuxetan |
| | | Brentuximab |
| | | Bretuximabvendontin |
| | | Trastuzumab emtansine |
| Hormones and hormone antagonists | | |
| | Gonadotropin releasing hormones (GcRH = LHRH) inhibitors | Tamoxifen |
| | | Fulvestrant |
| | Antiestrogen | Anastrozol letrozole |
| | SERMs = selective estrogen receptor modulators and | Exemestan |
| | SERDs = selective estrogen receptor downregulators | Abirateronacetat |
| | Aromatase inhibitors | Glucocorticoids |

TABLE 1-continued

Synergistic therapeutic groups, chemical groups and drug examples

| Therapeutic group | Chemical group | Drug example |
|---|---|---|
| | Gestagenes | |
| | Estrogenes | |
| | Antiandrogenes | |
| | Androgen-synthesis inhibitors | |
| Cytokine and cytokine network | | |
| Neutralizing free extracellular cytokine | TNFalfa receptor | Etanercept |
| | TNFalfa binding antibody | Infliksimab |
| | Vascular endothelial receptor binding antibody (VEGFR-antibody) | Bevacizumab |
| | Blocking binding of the cytokine receptor | Plerixafor |
| Cytokines | Granulocyte colony stimulating factor (G-CSF) | Methylated Filgrastim |
| | | Glycosylated Lenograstim |
| | Erythropoietin and darbepoietin | |
| | Interferon-alfa | IFN-alfa. |
| Antibodies towards immunological checkpoints | CTLA-4 | Ipilimumab |
| | PD-1 (programmed death receptor-1) | Nivolumab |
| | | Pembrolizumab |
| | | Lots of others in development including |
| | | Pidilizumab |
| | | AMP-224 (GlaxoSmithKline) |
| | | AMP-514 (GlaxoSmithKline) |
| | | PDR001 by Novartis |
| | | Cemiplimab by Regeneron and Sanofi. |
| | PD-L1 (Programmed death ligand 1 receptor) inhibitor | Atezolizumab |
| | | Avelumab |
| | | Durvalumab |
| | | Lots of others in development including |
| | | BMS-936559 and CK-301 |
| | Others as agonist towards CD40/CD40 ligands and antagonists towards TIM-3 and LAG-3 | |
| Oncolytic virus | Oncolytic virus | |
| Immunological adjuvants | Examples are | |
| | Cytokines | |
| | Polysaccharides as beta-glucans (f.x. lentinan) | |
| T-cell or dendritic therapy or NK-cell therapy or mesenchymal stem cell therapy | Increasing the level of T-cells with or without co-stimulation by chemotherapy, radiotherapy or therapy with small molecules. Increase level of cells that play a role in the native or adapted immune response as CD8+ T-cells, CD4+ T-cells, dendrite cells, macrophages. Transfection/transduction of malignant tumour specific T-cell receptors (TCR) or chimeric antigen receptors (CAR), bispecific CAR (BiTE), TCR (sTCR), NK-cells or mesenchymal stem cells | |
| Cancer vaccines | Examples: | |
| | Sipuleucel-T | Provenge |
| | T-VEC | Imlygic |

Cancer

The invention provides antibodies to YKL-40 and compositions of at least one YKL-40 antibody, such as two YKL-40 antibodies, such as three YKL-40 antibodies, such as five YKL-40 antibodies, which may be useful in methods of treating cancer. Furthermore, the invention relates to kits-of-parts and compositions for treatment of cancer.

In addition to classical cancers, non-cancer malignancies such as sarcomas and melanomas can also be treated according to the methods of the invention.

The cancer may for example be selected from the group consisting of breast-, colorectal-, pancreas-, bile duct-, stomach-, hepatocellular-, other gastrointestinal-, lung-, small cell lung-, ovarian-, uterine-, cervix-, testis-, prostate, bladder-, renal-, thyroid- and head/neck carcinoma, malignant melanoma, other skin cancers, neuroblastoma, glioblastoma, astrocytoma, malignant meningioma and other forms of brain cancer, osteosarcoma, chondrosarcoma, myosarcoma, fibrosarcoma and germ cell malignant tumours.

In a particular embodiment, the cancer is malignant melanoma. In another particular embodiment, the cancer is colon cancer.

Method of Treatment of Cancer

The present invention provides a method for treatment of cancer in an individual in need thereof.

In one embodiment, the invention provides a method for treating a cancer characterized by the presence of at least one solid neoplasm. Said method may comprise the steps of administering a therapeutically effective of one or more YKL-40 antibodies to an individual in need thereof and administering a therapeutically effective amount of an anti-cancer agent to said individual, thereby treating the cancer.

The YKL-40 antibody may in particular be any of the antibodies described herein above in the section "YKL-40 antibody".

The YKL-40 antibody may be formulated together with or separately from the anti-cancer agent. Thus, in one embodiment method may comprise administering a therapeutically effective amount of a composition comprising an YKL-40 antibody and an anti-cancer agent.

It is also comprised within the present invention that YKL-40 antibody and the anti-cancer agent may be linked covalently to each other.

In embodiments of the invention where the YKL-40 antibody and the anti-cancer agent are formulated separately they may be administered simultaneously or sequentially. Typically, it is preferred that said anti-cancer agent is administered simultaneously with or subsequent to the YKL-40 antibody.

In one embodiment, the YKL-40 antibody can be administered in combination with an anti-cancer agent. In another embodiment, the YKL-40 antibody is administered first to a patient in need thereof followed by administration of a cancer agent at a later time point. The YKL-40 antibody and anti-cancer agents can be administered multiple times in said individual either simultaneously or independently of each other. Thus, when the YKL-40 antibody and anti-cancer agents are administered separately, they may also be administered a different number of times.

The individual may be any individual suffering from or at risk of acquiring a cancer characterized by the presence of at least one solid neoplasm. In general the individual will be a mammal, and more preferably the individual will be a human being.

The YKL-40 antibody and anti-cancer agents can be administered by any suitable route known in the art. In general, the YKL-40 antibody is administered parenterally, for example by intravenous infusion. Other examples of routes of administration include intraperitoneal, intrathecal and intralymphatic. In some embodiments, administration may be by injection, e.g. subcutaneously.

The anti-cancer agent may be administered in any manner useful for the particular anti-cancer agent. Suitable modes of administration are known to the skilled person. Many anti-cancer agents are administered parenterally, for example by intravenous infusion. Other examples of routes of administration of anti-cancer agents include intraperitoneal, intrathecal and intralymphatic.

The dosage of antibody is dependent on several factors, for example the dosage could be in the range of 1 to 50 mg/kg, such as 4 to 10 mg/kg of anti YKL-40 antibody per kg body weight. In one embodiment, the antibody is administered to the subject in need thereof once or more than once. For example, the antibody may be administered more than once with an interval of in the range of a couple of days to several weeks.

Whilst it is possible for the YKL-40 antibody and the anti-cancer agents to be administered as raw compounds, it is preferred to present them in the form of a pharmaceutical formulation. The pharmaceutical formulation comprises the YKL-40 antibody and/or the anti-cancer agents and one or more pharmaceutically acceptable carriers. The pharmaceutical formulations may be prepared by conventional techniques, e.g. as described in Remington: The Science and Practice of Pharmacy 2013, Pharmaceutical Press.

The compounds of the present invention may be formulated in a wide variety of formulations for parenteral administration. For injections and infusions the formulations may take such forms as suspensions, solutions, or emulsions in oily or aqueous vehicles. Alternatively, the active ingredient may be in powder form for constitution before use with a suitable vehicle, e.g., sterile, pyrogen-free water. The formulations can be presented in unit-dose or multi-dose sealed containers, such as ampoules, vials, pre-filled syringes, infusion bags, or can be stored in a freeze-dried (lyophilized) condition requiring only the addition of the sterile liquid excipient, for example, water, for injections, immediately prior to use.

The formulations of the present embodiment may also include agents useful for pH maintenance, solution stabilization, or for the regulation of salt content and/or osmotic pressure.

The methods of the invention may be performed as the sole therapy, but frequently they are combined with other cancer therapies. The cancer may be treated by surgery and subsequently with the methods of the invention. The cancer may also be treated by irradiation as well as by the methods of the invention.

Items

The invention may further be defined by any one of the following items:

1. A composition comprising one or more antibodies specifically binding YKL-40, wherein at least one of the antibodies comprises at least one variable region comprising a CDR1, CDR2 and CDR3, wherein,
   a)
   CDR1 comprises or consists of an amino acid sequence of SEQ ID NO:5;
   CDR2 comprises or consists of an amino acid sequence of SEQ ID NO: 6; and
   CDR3 comprises or consists of an amino acid sequence of SEQ ID NO: 7; or
   b)
   CDR1 comprises or consists of an amino acid sequence of SEQ ID NO: 8;
   CDR2 comprises or consists of an amino acid sequence of SEQ ID NO: 9; and
   CDR3 comprises or consists of an amino acid sequence of SEQ ID NO: 10; or
   c)
   CDR1 of the light chain comprises or consists of an amino acid sequence of SEQ ID NO: 16;
   CDR2 of the light chain comprises or consists of an amino acid sequence of SEQ ID NO: 17;
   CDR3 of the light chain comprises or consists of an amino acid sequence of SEQ ID NO: 18;
   CDR1 of the heavy chain comprises or consists of an amino acid sequence of SEQ
   CDR2 of the heavy chain comprises or consists of an amino acid sequence of SEQ ID NO: 20; and
   CDR3 of the light chain comprises or consists of an amino acid sequence of SEQ ID NO: 21.
2. A composition comprising one or more antibodies specifically binding YKL-40, wherein at least one of the antibodies comprises at least one variable region comprising a CDR1, CDR2 and CDR3, wherein
   CDR1 comprising or consisting of an amino acid sequence of SEQ ID NO: 5 or SEQ ID NO: 8; and/or.
   CDR2 comprising or consisting of an amino acid sequence of the general formula: ISAXXGSTYY-ADSVKG (SEQ ID NO: 12), wherein X may be any amino acid and/or CDR3 comprising or consisting of an amino acid sequence of the general formula: XYNYXXWFDY (SEQ ID NO:13), wherein X may be any amino acid.
3. The composition according to any one of the preceding items, wherein the composition comprises two different antibodies specifically binding YKL-40.
4. The composition according to any one of the preceding items, wherein at least one antibody specifically binding YKL-40 comprises a variable region comprising a CDR1 comprising or consisting of an amino acid sequence of SEQ ID NO: 5.
5. The composition according to any one of the preceding items, wherein at least one antibody specifically binding YKL-40 comprises a variable region comprising a CDR1 comprising or consisting of an amino acid sequence of SEQ ID NO: 8.
6. The composition according to any one of the preceding items, wherein at least one antibody specifically binding YKL-40 comprises variable regions comprising a CDR1 of the light chain comprising or consisting of an amino acid sequence of SEQ ID NO: 16 and a CDR1 of the heavy chain comprising or consisting of an amino acid sequence of SEQ ID NO: 19.
7. The composition according to any one of the preceding items, wherein at least one antibody specifically binding YKL-40 comprising a variable region comprising a CDR2 comprising or consisting of an amino acid sequence of the general formula: ISAXXGSTYY-ADSVKG (SEQ ID NO: 12), wherein X may be any amino acid.
8. The composition according to any one of the preceding items, wherein at least one antibody specifically binding YKL-40 comprises a variable region comprising a CDR2 comprising or consisting of an amino acid sequence of SEQ ID NO: 6.
9. The composition according to any one of the preceding items, wherein at least one antibody specifically binding YKL-40 comprises a variable region comprising a CDR2 comprising or consisting of an amino acid sequence of SEQ ID NO: 9.
10. The composition according to any one of the preceding items, wherein at least one antibody specifically binding YKL-40 antibody comprises variable regions comprising a CDR2 of the light chain comprising or consisting of an amino acid sequence of SEQ ID NO: 17 and a CDR2 of the heavy chain comprising or consisting of an amino acid sequence of SEQ ID NO: 20.
11. The composition according to any one of the preceding items, wherein at least one antibody specifically binding YKL-40 comprises a variable region comprising a CDR3 comprising or consisting of an amino acid sequence of the general formula: XYNYXXWFDY (SEQ ID NO:13), wherein X may be any amino acid.
12. The composition according to any one of the preceding items, wherein at least one antibody specifically binding YLK-40 comprises a variable region comprising a CDR3 comprising or consisting of an amino acid sequence of SEQ ID NO: 7.
13. The composition according to any one of the preceding items, wherein at least one antibody specifically binding YLK-40 comprises a variable region comprising a CDR3 comprising or consisting of an amino acid sequence of SEQ ID NO: 10.
14. The composition according to any one of the preceding items, wherein at least one antibody specifically binding YLK-40 antibody comprises variable regions comprising a CDR3 of the light chain comprising or consisting of an amino acid sequence of SEQ ID NO: 18 and a CDR3 of the heavy chain comprising or consisting of an amino acid sequence of SEQ ID NO: 21.
15. The composition according to any one of the preceding items, wherein the antibody comprises two or more different variable regions, wherein each variable region may be fused to a constant region, e.g. to Fc regions.
16. The composition according to any one of the preceding items, wherein at least one antibody specifically binding YKL-40 comprises a variable region comprising a CDR1, CDR2 and CDR3, wherein,
    CDR1 comprises or consists of an amino acid sequence of SEQ ID NO:5;
    CDR2 comprises or consists of an amino acid sequence of SEQ ID NO: 6; and
    CDR3 comprises or consists of an amino acid sequence of SEQ ID NO: 7.
17. The composition according to any one of the preceding items, wherein at least one antibody specifically binding YKL-40 comprises a variable region comprising a CDR1, CDR2 and CDR3, wherein,
    CDR1 comprises or consists of an amino acid sequence of SEQ ID NO: 8;
    CDR2 comprises or consists of an amino acid sequence of SEQ ID NO: 9; and
    CDR3 comprises or consists of an amino acid sequence of SEQ ID NO: 10.
18. The composition according to any one of the preceding items, wherein at least one antibody specifically binding YLK-40 antibody comprises or consists of a variable region comprising or consisting of an amino acid sequence of SEQ ID NO:3.
19. The composition according to any one of the preceding items, wherein at least one antibody specifically binding YLK-40 antibody comprises or consists of a variable region comprising or consisting of an amino acid sequence of SEQ ID NO:4.
20. The composition according to any one of the preceding items, wherein the variable region(s) are linked to an Fc region, optionally via a linker.
21. The composition according to any one of the preceding items, wherein said antibody specifically binding YKL-40 comprises two variable regions, wherein each variable region is linked to an Fc region, optionally by a linker.
22. The composition according to item 21, wherein said Fc regions are linked to each other.
23. The composition according to item 21, wherein said Fc regions are linked together by disulphide bonds.
24. The composition according to any one of the preceding items, wherein at least one antibody specifically binding YLK-40 consists of a variable region consisting of the amino acid sequence SEQ ID NO:3 linked to an Fc region, wherein said antibody optionally forms dimers.
25. The composition according to any one of the preceding items, wherein at least one antibody specifically binding YLK-40 consists of a variable region consisting of the amino acid sequence SEQ ID NO:4 linked to an Fc region, wherein said antibody optionally forms dimers.
26. The composition according to any one of the preceding items, wherein the Fc region is a constant region of IgE, for example an Fc region of SEQ ID NO:61.

27. The composition according to any one of the preceding items, wherein the Fc region is a human Fc region.

28. The composition according to any one of the preceding items, wherein at least one antibody specifically binding, wherein the Fc region comprises or consists of amino acid sequence SEQ ID NO: 22 or SEQ ID NO: 23 or SEQ ID NO:62.

29. The composition according to any one of the preceding items, wherein at least one antibody specifically binding YKL-40 antibody comprises or consists of variable regions comprising a CDR1, CDR2 and CDR3, wherein,
    CDR1 of the light chain comprises or consists of an amino acid sequence of SEQ ID NO: 16;
    CDR2 of the light chain comprises or consists of an amino acid sequence of SEQ ID NO: 17;
    CDR3 of the light chain comprises or consists of an amino acid sequence of SEQ ID NO: 18;
    CDR1 of the heavy chain comprises or consists of an amino acid sequence of SEQ ID NO: 19;
    CDR2 of the heavy chain comprises or consists of an amino acid sequence of SEQ ID NO: 20; and
    CDR3 of the light chain comprises or consists of an amino acid sequence of SEQ ID NO: 21.

30. The composition according to any one of the preceding items, wherein at least one antibody specifically binding YLK-40 antibody comprises a light chain variable region comprising or consisting of an amino acid sequence of SEQ ID NO: 14 and a heavy chain variable region comprising or consisting of amino acid sequence of SEQ ID NO: 15.

31. The composition according to any one of the preceding items, wherein at least one antibody specifically binding YKL-40 is capable of binding an epitope present in both human and murine YKL-40.

32. The composition according to any one of the preceding items, wherein at least one antibody specifically binding YKL-40 is capable of binding the same YKL-40 epitope bound by any of the antibodies defined in any one of the preceding items.

33. The composition according to any one of the preceding items, wherein at least one antibody specifically binding YKL-40 binds the same YKL-40 epitope bound by the antibodies of item 18.

34. The composition according to any one of the preceding items, wherein at least one antibody specifically binding YKL-40 binds the same YKL-40 epitope bound by the antibodies of item 19.

35. The composition according to any one of the preceding items, wherein at least one antibody specifically binding YKL-40 binds the same YKL-40 epitope bound by the antibodies of item 29.

36. The composition according to any one of the preceding items, wherein the composition comprises at least two different antibodies specifically binding YLK-40, wherein said antibodies are as defined in any one of the preceding items.

37. The composition according to any one of the preceding items, wherein the composition comprises one antibody with a variable region comprising a CDR1, CDR2 and CDR3, wherein,
    CDR1 comprises or consists of an amino acid sequence of SEQ ID NO:5;
    CDR2 comprises or consists of an amino acid sequence of SEQ ID NO: 6; and
    CDR3 comprises or consists of an amino acid sequence of SEQ ID NO: 7;
    and another antibody with a variable region comprising a CDR1, CDR2 and CDR3, wherein,
    CDR1 comprises or consists of an amino acid sequence of SEQ ID NO: 8;
    CDR2 comprises or consists of an amino acid sequence of SEQ ID NO: 9; and
    CDR3 comprises or consists of an amino acid sequence of SEQ ID NO: 10.

38. The composition according to any one of the preceding items, wherein the composition comprises one antibody comprising a variable region comprising a CDR1, CDR2 and CDR3, wherein,
    CDR1 comprises or consists of an amino acid sequence of SEQ ID NO:5;
    CDR2 comprises or consists of an amino acid sequence of SEQ ID NO: 6; and
    CDR3 comprises or consists of an amino acid sequence of SEQ ID NO: 7;
    and another antibody with variable region(s) comprising a CDR1, CDR2 and CDR3, wherein, CDR1 of the light chain comprises or consists of an amino acid sequence of SEQ ID NO: 16;
    CDR2 of the light chain comprises or consists of an amino acid sequence of SEQ ID NO: 17;
    CDR3 of the light chain comprises or consists of an amino acid sequence of SEQ ID NO: 18;
    CDR1 of the heavy chain comprises or consists of an amino acid sequence of SEQ ID NO: 19;
    CDR2 of the heavy chain comprises or consists of an amino acid sequence of SEQ ID NO: 20; and
    CDR3 of the light chain comprises or consists of an amino acid sequence of SEQ ID NO: 21, 39. The composition according to any one of the preceding items, wherein the composition comprises one antibody comprising a variable region comprising a CDR1, CDR2 and CDR3, wherein,
    CDR1 comprises or consists of an amino acid sequence of SEQ ID NO: 8;
    CDR2 comprises or consists of an amino acid sequence of SEQ ID NO: 9; and
    CDR3 comprises or consists of an amino acid sequence of SEQ ID NO: 10; and another antibody comprising variable regions comprising a CDR1, CDR2 and CDR3, wherein, CDR1 of the light chain comprises or consists of an amino acid sequence of SEQ ID NO: 16;
    CDR2 of the light chain comprises or consists of an amino acid sequence of SEQ ID NO: 17;
    CDR3 of the light chain comprises or consists of an amino acid sequence of SEQ ID NO: 18;
    CDR1 of the heavy chain comprises or consists of an amino acid sequence of SEQ ID NO: 19;
    CDR2 of the heavy chain comprises or consists of an amino acid sequence of SEQ ID NO: 20; and
    CDR3 of the light chain comprises or consists of an amino acid sequence of SEQ ID NO: 21.

40. The composition according to any one of the preceding items, wherein the composition comprises a bi- or multispecific antibody comprising one or more variable regions comprising a CDR1 of SEQ ID NO: 5, a CDR2 of SEQ ID NO: 6 and a CDR3 of SEQ ID NO:7 and one or more variable regions comprising a CDR1 of SEQ ID NO: 8, a CDR2 of SEQ ID NO: 9 and a CDR3 of SEQ ID NO: 10.

41. The composition according to any one of the preceding items, wherein the composition comprises a bi- or multispecific antibody comprising one or more variable regions comprising a CDR1 of SEQ ID NO: 5, a CDR2 of SEQ ID NO: 6 and a CDR3 of SEQ ID NO:7 and one or more variable regions made up of a $V_L$ and $V_H$, wherein the $V_L$ comprises a CDR1 of SEQ ID NO: 16, a CDR2 of SEQ ID NO: 17 and a CDR3 of SEQ ID NO: 18, and the $V_H$ comprises a CDR1 of SEQ ID NO: 19, a CDR2 of SEQ ID NO: 20 and a CDR3 of SEQ ID NO:21.

42. The composition according to any one of the preceding items, wherein the composition comprises a bi- or multispecific antibody comprising one or more variable regions comprising CDR1 of SEQ ID NO: 8, a CDR2 of SEQ ID NO: 9 and a CDR3 of SEQ ID NO: 10 and one or more variable regions made up of a $V_L$ and $V_H$, wherein the $V_L$ comprises a CDR1 of SEQ ID NO: 16, a CDR2 of SEQ ID NO: 17 and a CDR3 of SEQ ID NO: 18, and the $V_H$ comprises a CDR1 of SEQ ID NO: 19, a CDR2 of SEQ ID NO: 20 and a CDR3 of SEQ ID NO:21.

43. The composition according to any one of the preceding items, wherein the composition comprises a bi- or multispecific antibody comprising one or more variable regions comprising or consisting of SEQ ID NO: 3 and one or more variable regions comprising or consisting of SEQ ID NO:4.

44. The composition according to any one of the preceding items, wherein the composition comprises at least two different antibodies specifically binding YLK-40, wherein the first antibody is an antibody as defined in any one of items 4, 7, 8, 11, 16, 18, 24 or 33 and the second antibody is an antibody as defined in any one of items 5, 7, 9, 13, 17, 19, 25 or 34.

45. A method of treating disease associated with expression of YKL-40, the method comprising administering a therapeutically effective amount of the composition or the kit-of-parts according to any one of the preceding items to a subject in need thereof.

46. The method according to item 45, wherein the method further comprises administration of an anti-cancer agent.

47. A composition or kit-of-parts according to any one of items 1 to 44 for use in a method of treating a disease associated with YKL-40 expression.

48. The method, composition for use or the use according to any one of items 45 to 47, wherein the disease is cancer.

49. The method, composition for use or the use according to any one of items 45 to 47, wherein the disease is an inflammatory disease.

50. The method or the composition for use according to any one of items 45 to 48, wherein the disease is arthritis, such as osteoarthritis.

51. The method or the composition for use according any one of items 45 to 50, wherein the method comprises administering a therapeutically effective amount of two different YKL-40 antibodies to a subject in need thereof, wherein said antibodies are as defined in any one of the preceding items.

52. The method or the composition for use according any one of items 45 to 51, wherein the method comprises administering a therapeutically effective amount of two different YKL-40 antibodies to a subject in need thereof, wherein said antibodies are as defined in any one of the preceding items, wherein said antibodies are administered simultaneously or sequentially.

53. The method, composition for use or the use according to any one of items 45 to 52, wherein the composition or kit-of-parts comprises two different YKL-40 antibodies, wherein said antibodies are as defined in any one of the preceding items.

54. The method or the composition for use according any one of items according to any one of items 51 to 53, whereby the two antibodies comprises or consists of amino acid sequences SEQ ID NO:3 or SEQ ID NO: 4.

55. The method or the composition according to any one of items 45 to 54, wherein the method is a method for inhibiting the progression of cancer.

56. The method or the composition according to any one of items 45 to 55, wherein the anti-cancer agent is selected from the group consisting of a chemotherapeutic agent, an immunotherapeutic agent, checkpoint inhibitors, anti-cancer antibodies, and cytostatic small molecule.

57. The method or the composition according to any one of items 45 to 56, wherein the anti-cancer agent is a chemotherapeutic agent.

58. The method or the composition according to any one of items 45 to 56, wherein the anti-cancer agent is platinum containing cytotoxic compound, such as a square planar coordination complex of platinum.

59. The method or the composition according to any one of items 45 to 58, wherein the anti-cancer agent is cisplatin.

60. The method or composition according to any one of items 45 to 59, wherein the anti-cancer agent is a radioactive substance, such as radioactive iodine.

EXAMPLES

Example 1: Selection of Phage Antibodies B3 and B10 Recognizing YKL-40

Aim:

To select antibodies, which recognize human and murine YKL-40.

Materials and Methods:

YKL-40 Protein hYKL-40 protein was obtained from the supernatant of MG63 cells or was purchased from Biotech (Catalogue #2599-CH). MG63 production flasks were seeded at $1.8 \times 10^4$ cells/cm$^2$ in RPMI-40 (Irvine Scientific) plus newborn calf serum, 100 mL/L (Irvine Scientific), 0.1 mol/L HEPES, and 50 mg/L vitamin C (complete medium). Flasks were incubated at 37° C. with humidity and CO2-enriched (100 mL/L) atmosphere for 6-8 days, replacing spent medium with fresh every 2-3 days. The cultures were then switched to serum-free medium (complete medium minus the newborn calf serum). The supernatants were harvested and the media replaced every 1-3 days for 30 days. hYKL-40 protein was purified from the supernatants by concentrating glass-fiber-filtered material 20-fold with a 30-kDa screen channel cassette with tangential flow (Filtron) and then affinity-purifying over a heparin-Sepharose CL-6B column (Pharmacia Biotech) equilibrated with a solution of 10 mmol/L sodium phosphate and 50 mmol/L sodium chloride, pH 7.5. Bound material was eluted with a sodium chloride gradient (from 50 mmol/L to 2 mol/L) in 10 mmol/L sodium phosphate, pH 7.5, and 4-mL fractions were collected and pooled according to: absorbance at 280 nm, hYKL-40 protein concentration by immunoassay and purity by sodium dodecyl sulfate-polyacrylamide gel electrophoresis. mYKL-40 were purchased from Biotech (Catalogue #: 2649-CH). Alternatively, mYKL-40 can be obtained from supernatant of the mouse myeloma cell line NS0.

Phage Rescue

Selection of phage antibodies recognizing YKL-40 were performed using a predator antibody library, which is a single scaffold domain library with variation in CDR2 and CDR3 (Mandrup, Friis et al. 2013) against the purified YKL-40 protein. Thus, the antibodies of this library are single domain antibodies.

First a plastic immunotube was coated overnight with YKL-40 at 4° C., so the antigen could be partially absorbed by the plastic and anchored to the inner surface of the tube. The day after the tube was washed 5 times with PBS and incubated with 2% BSA in PBS for 2 hours at room temperature (RT). After another round of washing, 100 µl of the phage antibody library PREDATOR was added in 4 ml of 2% BSA in PBS. The phage antibody library was incubated for 60 min at RT rotating using an under- and over turntable and then further 60 min at RT standing on the bench. Unbound phages were washed away with 10 washes in PBS containing 0.1% Tween 20 and 10 washes with PBS.

Bound phages were eluted by adding 500 µl of trypsin-PBS (50 µl of 10 mg/ml trypsin stock solution added to 450 µl PBS) and incubating on rotating for 10 min at RT. The eluent was then incubated with 10 ml of TG1 (*E. coli*) in exponential growth (at an OD 600 of 0.4) for 30 min at 37° C. The bacteria were then plated on TYE plates containing 100 µg/ml ampicillin and 1% glucose and grown overnight at 30° C. The following day individual colonies from the plates were picked up with a toothpick for monoclonal phage antibody rescue and the remaining bacteria were scraped into 2×TY media containing 100 µg/ml ampicillin and 1% glucose for polyclonal rescue. The monoclonal picked colonies were put in a well of a 96 cell-well plate containing 2×TY medium with 100 µg/ml ampicillin and 1% glucose and grown on a shaker overnight at 37° C. The day after a transfer device was used to transfer a small inoculum from this plate (the master plate) to a second 96 cell-well plate containing the same medium. Bacteria were grown shaking at 37° C. for 2 hours, new medium containing Helper phage, KM13 was added. The plate were incubated for 1 hour at 37° C. to let the Helper infect the cell, after this media was changed to 2×TY medium containing 100 µg/ml Ampicillin and 50 µg/ml of Kanamycin, finally the bacteria were incubate at 30° C., on shaking, overnight. The supernatant was used for ELISA. The polyclonal scraped bacteria were grown shaking at 37° C. for 2 hours, new medium containing Helper phage, KM13 was added. The plates were incubated for 1 hour at 37° C. to let the Helper infect the cell, after this media was changed to 2×TY medium containing 100 µg/ml Ampicillin and 50 µg/ml of Kanamycin, finally the bacteria were incubate at 30° C., on shaking, overnight. The phage antibodies produced in the media were precipitated by adding ¼ volume of a solution containing 20% PEG 6000 and 2.5 M NaCl. The precipitated phage were used for successive rounds of selection. In successive rounds of selection human and murine YKL40 were used for selection to allow phage antibodies binding both to be enriched.

Screening Rounds

Preliminary Screening

After selection the eluted phages were infected in the *E. coli* TG-1 and spread on Amp selective agar plates. Around 500 colonies were obtained. These were inoculated in 100 µl 2×TY in 96 well plates. Phage antibodies were produced from the plates using the helper phage KM13 according to standard procedures.

Example of Preliminary Screening

After coating with used (MG63 conditioned) or fresh media, the ELISA plates were blocked with 2% skimmed milk powder in PBS. After blocking 50 µl of the phage supernatant was added to each well and incubated. The plates were washed and incubated with 1:5000 diluted anti-M13 antibody (HRP conjugated). After washing the ELISA plate were developed using TMB and the plate read in an ELISA reader.

Dilution Series of the PEG Precipitated Phages

Selected clones which were judged potential positive in the preliminary screening were grown in 50 ml culture and rescued using the KM13 helper phage. After overnight growth the supernatant were PEG precipitated according to standard procedures, and the pellet resuspended in 1 ml PBS. As phage antibody concentration is highly enriched by growing in 50 ml baffled flasks, the phage antibody concentration after PEG precipitation is 100-1000 more concentrated compared to the initial screen.

The PEG precipitated phage were used in validating ELISA, were a dilution series of the PEG precipitated phage were applied to ELISA plates coated with MG63 conditioned media or Fresh media. ELISA was performed as above.

Secondary Screening-Validation of Binding to YKL-40

After phage rescue supernatants containing selected single-domain antibodies were applied in ELISA to test for binding to YKL-40. Serum free media (RPMI 1640 with 1% Non-essential amino acids) were conditioned by growing MG63 cell line for 4 days. The supernatant was coated in ELISA plates. Fresh media without conditioning with MG63 were used as controls.

An ELISA was performed with the PEG precipitated phage from above (obtained under the section "Dilution series of the PEG precipitated phages"):

In the first round the plate was coated using conditioned MG63 media containing hYKL-40

In the second round the plate was coated with 0.5 µg purified mYKL-40

The ELISA was performed as above. The results are shown in Table 2 below. The numbers (1-12) on the top and the letter (A-H) on the left indicate the tested phages and their corresponding well.

Sequencing of Antibodies

All the clones validated to bind to YKL-40 were next sequenced.

Cloning

The two clones B3 (SEQ ID NO: 3) and B10 (SEQ ID NO: 4) can be cloned into a vector pFuse-hIgE as described in Moutel et al., 2009, or a vector containing another immunoglobulin constant part. The vectors can be transfected into a suitable cell, such as ExpiCHO cells and expressed in this cell. This transfection leads to antibodies of $V_H$ domains fused to human IgE or other Fc regions expressed by the vector.

After transient transfection of suitable cells with the expression plasmid, secreted antibodies can be purified from the supernatant.

Results

Monoclonal ELISA from individual colonies from titration plates after selection using predator library (first round selection against hYKL-40 and second round selection against m YKL-40) are provided in Table 2. The OD obtained after the second round of screening is shown in table 2, where a higher number indicates increased binding.

TABLE 2

|   | 1     | 2     | 3     | 4     | 5     | 6     | 7     | 8     | 9     | 10    | 11    | 12    |
|---|-------|-------|-------|-------|-------|-------|-------|-------|-------|-------|-------|-------|
| A | 1.356 | 0.095 | 0.175 | 0.734 | 1.024 | 0.098 | 0.211 | 0.533 | 0.25  |       | 0.087 | 0.086 | 0.09 |
| B | 0.161 | 0.512 | 1.466 | 0.132 | 0.096 | 0.117 | 0.242 | 0.117 | 0.12  |       | 1.922 | 0.096 | 0.205 |
| C | 0.341 | 0.161 | 0.078 | 1.665 | 0.442 | 0.572 | 0.242 | 0.316 | 0.158 |       | 0.113 | 0.087 | 0.342 |
| D | 0.249 | 1.289 | 0.109 | 0.184 | 0.183 | 1.016 | 1.902 | 0.336 | 0.1   |       | 0.079 | 0.384 | 0.32 |
| E | 0.531 | 0.097 | 0.374 | 1.123 | 1.379 | 0.084 | 0.579 | 0.081 | 0.231 |       | 0.841 | 0.087 | 0.855 |
| F | 0.11  | 0.301 | 1.015 | 0.77  | 0.196 | 0.315 | 0.967 | 0.091 | 0.1   |       | 0.522 | 0.204 | 0.257 |
| G | 1.897 | 0.116 | 0.657 | 0.098 | 0.709 | 0.522 | 0.146 | 0.096 | 0.837 |       | 0.597 | 1.838 | 0.472 |
| H | 0.103 | 0.304 | 0.992 | 0.118 | 0.234 | 0.344 | 0.744 | 0.131 | 1.289 |       | 0.956 | 0.162 | 0.203 |

Conclusion

Several antibodies had a value over 1. B3 (SEQ ID NO: 3) and B10 (SEQ ID NO: 4) bind to purified human and murine YKL-40 and were selected as the best candidates.

Example 2: B3-hFc does not Bind a Linear Epitope of YKL-40

Aim:
To investigate if B3 (SEQ ID NO: 3) fused to a human Fc (hFc) (referred to as B3-hFc) bind human and murine YKL-40. The sequence of the human Fc is provided herein as SEQ ID NO: 23.
Western Blot:
First, samples for the western blot were prepared. Therefore, 1.04 µl (0.5 µg) hYKL-40 were mixed with 2.5 µl 4× sample buffer, 1 µl 1 M DTT and 5.46 µl water. 5 µl (0.5 µg) mYKL-40 were mixed with 2.5 µl 4× sample buffer, 1 µl 1 M DTT and 1.5 µl water. As a negative control, 5 µl PBS were mixed with 2.5 µl 4× sample buffer, 1 µl 1 M DTT and 1.5 µl water. As a positive control, 3 µl mouse anti-vimentin antibody (Sigma Aldrich, V6389) was mixed with 2.5 µl 4× sample buffer, 1 µl 1 M DTT and 3.5 µl water. Afterwards, the samples were heated at 95° C. for 10 min and the samples were loaded on a 4-20% SurePAGE, Bis-TRIS gel. The gel was run at 120V for 70 min and afterwards the samples were transferred to a nitrocellulose membrane using iBlot system. The membrane was blocked over night at 4° C. in PBS with 0.1% Tween and washed at the next day three times with PBST. The membrane was incubated with 1 µg/ml primary antibody B3-hFc in PBS with 0.1% Tween for 2 h at RT. Afterwards, the membrane was washed again three times with PBS with 0.1% Tween and incubated with a HRP conjugated anti-mouse or anti-human secondary antibody for 2 h at RT. After washing the blot another 3 times with PBS and 0.1% Tween, the western blot was developed with detection reagent.
Dot Blot:
A dot blot was performed by adding 0.4 µg and 0.2 µg of hYKL-40, 0.4 µg and 0.2 µg mYKL-40, 0.4 µg and 0.2 µg of calmodulin (negative control) and PBS (negative control) onto the nitrocellulose membrane. The area that the solution penetrates was minimized. The membrane was dried for 1 h at room temperature (RT). Afterwards the membrane was blocked in PBS with 0.1% Tween overnight at 4° C. followed by three washing steps with PBS with 0.1% Tween. The membrane was incubated with B3-hFc (1 µg/mL) in blocking buffer for 2 h at RT in a shaker followed by three washing steps with PBS with 0.1% Tween. The membrane was incubated with HRP anti-human secondary antibody for 2 hours at RT in shaker followed by three washing steps with PBS with 0.1% Tween. The western blot was developed with western blotting detection reagent.

Results

Figure 2:
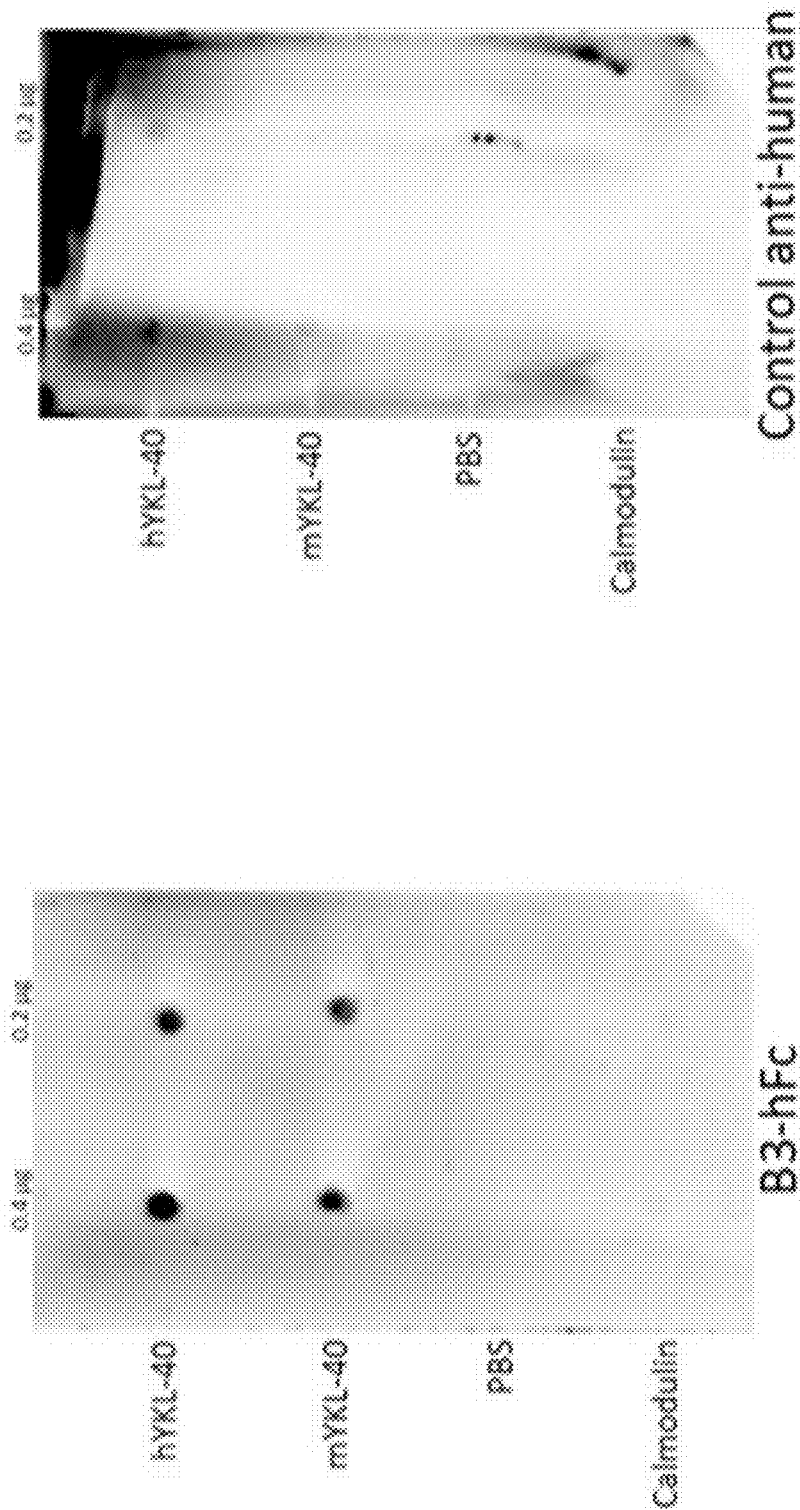
FIG. 2 shows, that B3 (SEQ ID NO: 3) binds to both human and mouse YKL-40, but does not bind to calmodulin (FIG. 3). A dot blot was performed by adding 0.4 µg and 0.2 µg of hYKL-40, 0.4 µg and 0.2 µg mYKL-40, 0.4 µg and 0.2 µg of calmodulin (negative control) and PBS (negative control) onto the nitrocellulose membrane. The membrane was incubated with B3 (SEQ ID NO: 3)-hFc.

The dot blot results indicate that B3 (SEQ ID NO: 3) fused to human Fc (hFc) binds to both human and mouse YKL-40, but does not bind to calmodulin (FIG. 2). The antibody did not appear to bind to a linear epitope, and it is thus believed that B3 (SEQ ID NO: 3)-hFc likely binds to a conformational epitope of both human and mouse YKL-40.

Example 3: B10 Binds Human and Murine YKL-40

Aim:
To investigate if B10 (SEQ ID NO: 4) fused to a human Fc (referred to as B10-hFc) bind to human and murine YKL-40. The sequence of the human Fc is provided herein as SEQ ID NO: 23.
Material and Methods:
The western blot was performed according to the description in Example 2 except, that the western blot was incubated with B10-hFc.

Results

B10-hFc binds to both human and mouse YKL-40 (FIG. 3). It appears that B10-hFc binds to a linear epitope of both human and mouse YKL-40.

Example 4: B3 and B10 Bind to mYKL-40

Aim:
To investigate if B3 (SEQ ID NO: 3) fused to murine Fc (mFc)(herein referred to as B3-mFc) and B10 (SEQ ID NO: 4) fused to mFC (herein referred to as B10-mFc) bind to murine YKL-40. The sequence of the murine Fc is provided herein as SEQ ID NO: 62.
Material and Methods:
A 96-well ELISA plate was coated overnight at RT with 100 µl per well of 2.5 µg/ml mYKL-40 or 2.5 µg/ml calmodulin as control. Afterwards, the wells were washed three times with PBS and blocked with 200 µl Casein per well for 2 h at RT. After another three times washing with PBS, 100 µl of primary antibody B3-mFc or B10-mFc at different concentrations were added for 1 h at RT. The concentrations were 0.25 µg/ml, 0.5 g/ml, 1 µg/ml, 2.5 µg/ml, 6.25 µg/ml, 12.5 µg/ml, 15 µg/ml and 20 µg/ml. Subsequently, the wells were washed 3 times with PBS with 0.1% Tween before 100 µl of HRP conjugated anti-mouse secondary antibody were added for 1 h at RT. After another three times washing with PBS with 0.1% Tween, 100 µl of substrate solution TMB were added to each well till a blue colour is developed. The reaction was stopped by adding 450 µl 1 M sulphuric acid. The OD was read at 650 nm and 450 nm. Subsequently the OD 650 were subtracted from OD 450.

Results

Figure 4:
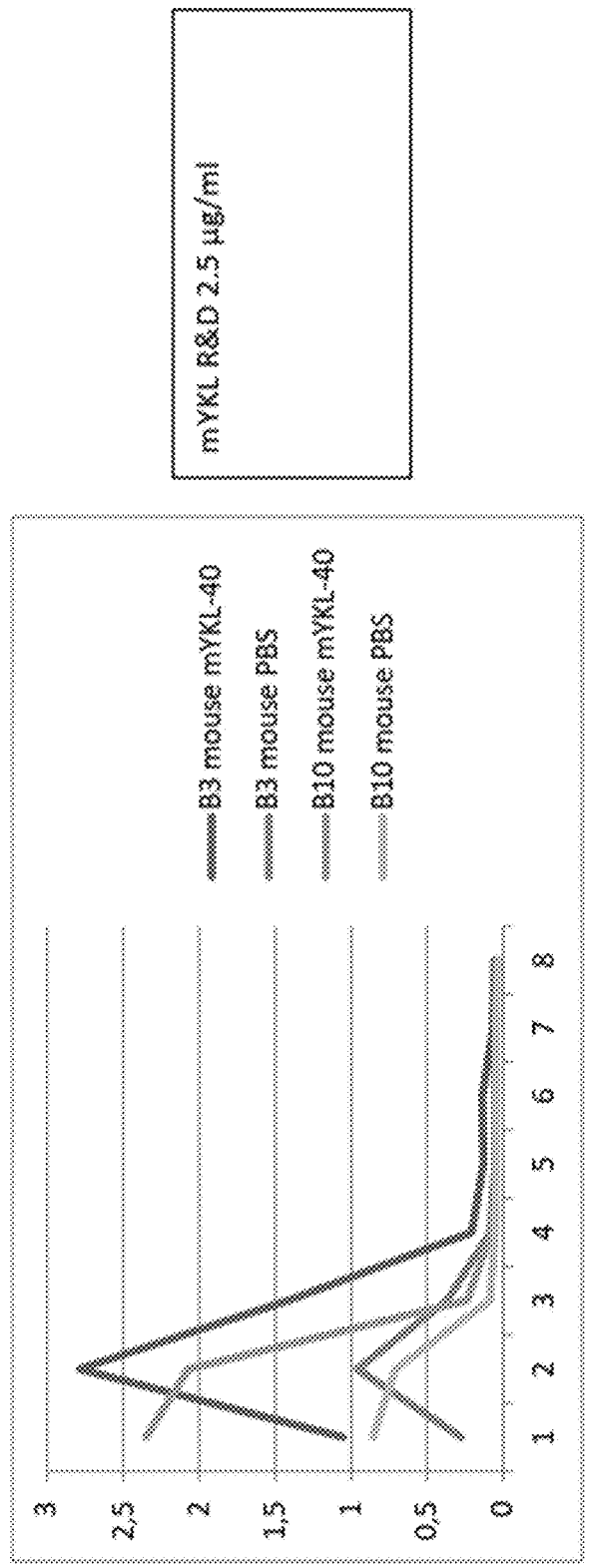
FIG. 4 shows, that B3 (SEQ ID NO: 3) fused to a murine Fc region (mFc)(B3 mouse) and B10 (SEQ ID NO: 4) fused to a mFc (B10 mouse) bind to murine YKL-40 (mYKL-40). A 96-well ELISA plate was coated with 2.5 µg/ml mYKL-40 or 2.5 µg/ml calmodulin as control. 0.25 µg/ml (8), 0.5 µg/ml (7), 1 µg/ml (6), 2.5 µg/ml (5), 6.25 µg/ml (4), 12.5 g/ml (3), 15 µg/ml (2) and 20 µg/ml (1) of the antibodies B3 (SEQ ID NO: 3)-mFc or B10 (SEQ ID NO: 4)-mFc were added.

B3-mFc and B10-mFc bind to mYKL-40 (FIG. 4).

Example 5: B3 and B10 Bind to hYKL-40

Aim:

To investigate if B3 (SEQ ID NO: 3) fused to mFc (herein referred to as B3-mFc) and B10 (SEQ ID NO: 4) fused to mFc (herein referred to as B10-mFc) bind to human YKL-40.

Material and Methods:

The ELISA was performed according to example 1. hYKL-40 was used to coat the ELISA plate.

Results

Figure 5:
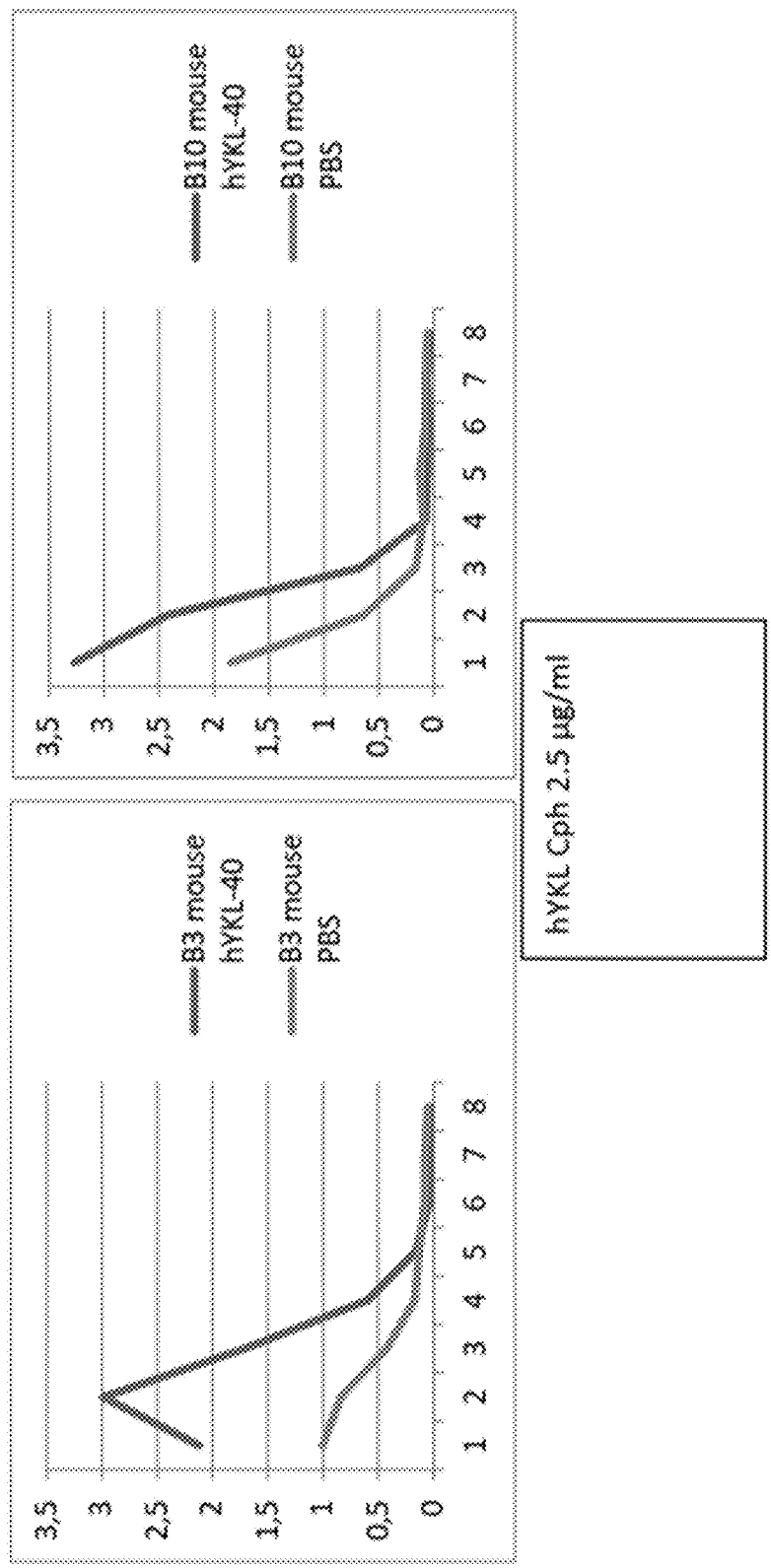
FIG. 5 shows, that B3 (SEQ ID NO: 3) fused to a murine Fc (mFc)(B3 mouse) and B10 (SEQ ID NO: 4) fused to mFc (B10 mouse) bind to human YKL-40 (hYKL-40). A 96-well ELISA plate were coated with 2.5 µg/ml hYKL-40 or 2.5 µg/ml calmodulin as control. 0.25 µg/ml (8), 0.5 g/ml (7), 1 µg/ml (6), 2.5 µg/ml (5), 6.25 µg/ml (4), 12.5 µg/ml (3), 15 µg/ml (2) and 20 µg/ml (1) of the antibodies B3 (SEQ ID NO: 3)-mFc or B10 (SEQ ID NO: 4)-mFc were added.

B3 (SEQ ID NO: 3)-mFc and B10 (SEQ ID NO: 4)-mFc bind to hYKL-40 (FIG. 5).

Conclusion

The inventors of the present disclosure have realized that B3 (SEQ ID NO:3)-mFc and B10 (SEQ ID NO:4)-mFc are able to bind hYKL-40.

Example 6: 201F9 Binds to hYKL-40 but not the Same Epitope as B3 (SEQ ID NO: 3) and B10 (SEQ ID NO: 4)

Aim:

It was investigated if the YKL-40 antibody named 201F9 binds hYKL-40 and if it binds to the same epitopes as B3-hFc and B10-hFc.

Material and Methods:

The competitive ELISA was performed essentially as described in example 5 with the exception, that first 2.5 µg/ml 201F9 were added into the wells for 1 h at RT before the wells were washed three times with PBS with 0.1% Tween and B3-hFc or B10-hFc were added in different concentrations.

Results

Figure 6:
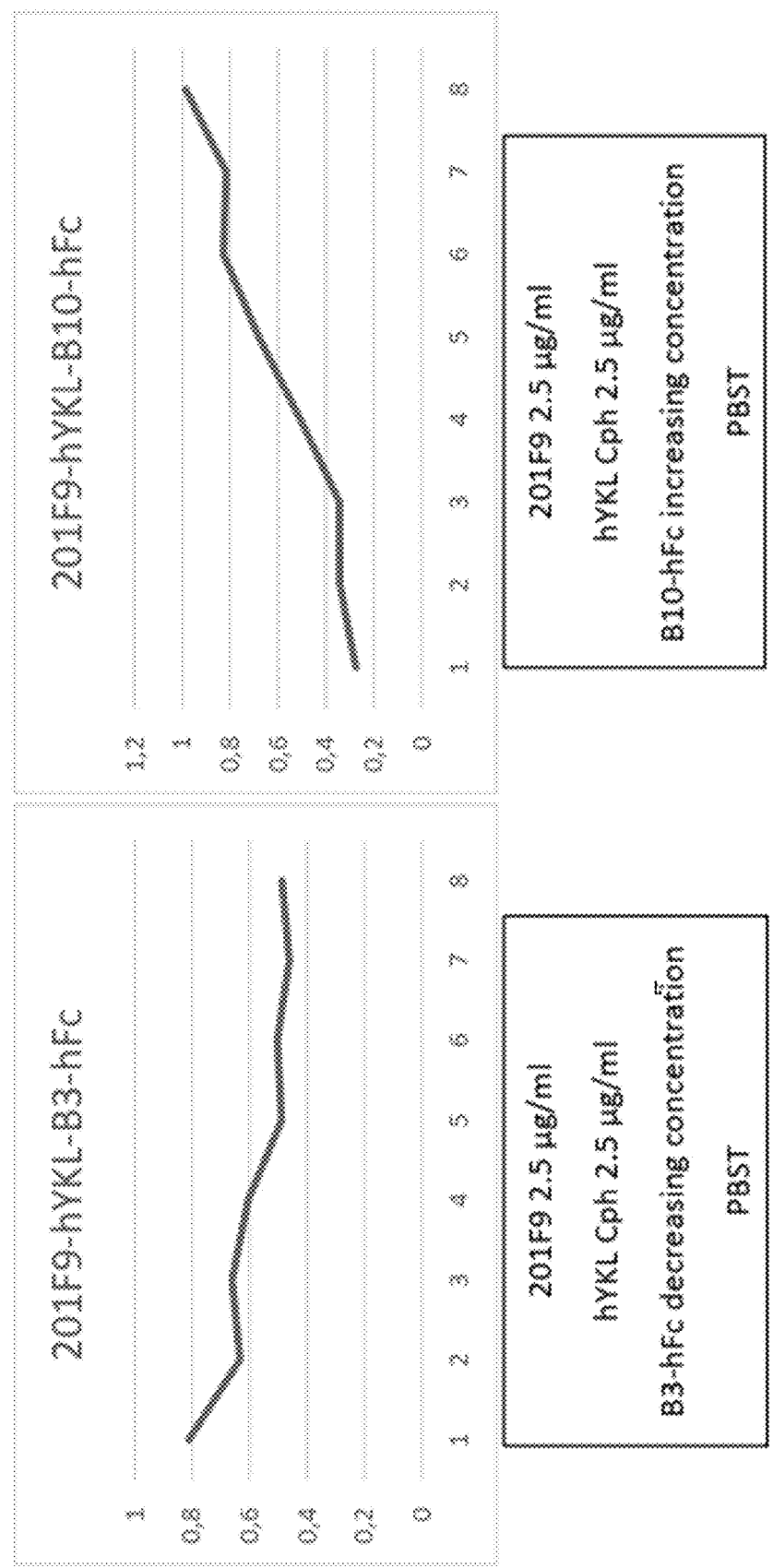
FIG. 6 shows, that YKL-40 antibody 201F9 binds hYKL-40 at a different epitope than B3 (SEQ ID NO: 3)-hFc or B10 (SEQ ID NO: 4)-hFc. The competitive ELISA was performed by first adding 2.5 µg/ml 201F9 before the wells were washed three times and B3 (SEQ ID NO: 3)-hFc or B10 (SEQ ID NO: 4)-hFc added in different concentrations.
Figure 7:
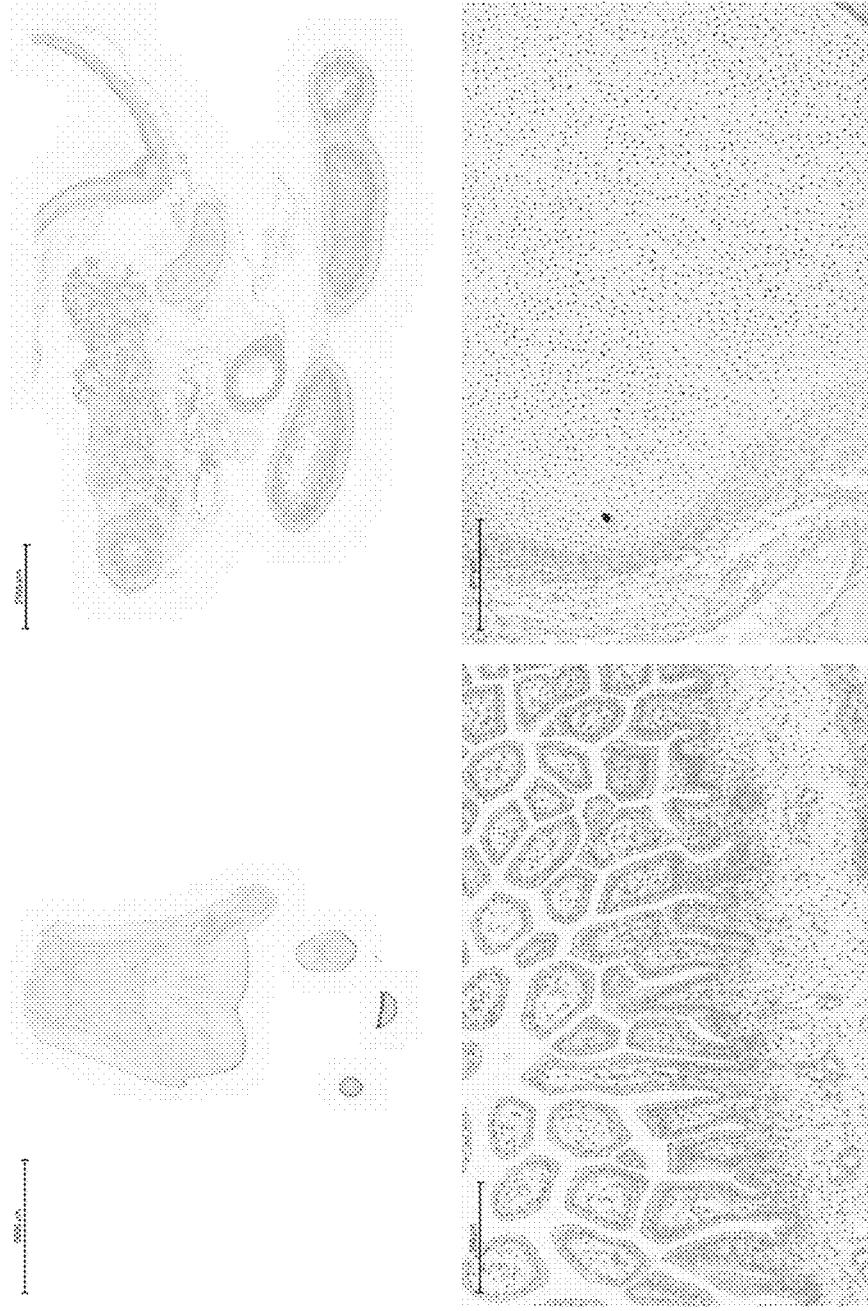
FIG. 7: H7 (comprising $V_L$ of SEQ ID NO: 14 and $V_H$ of SEQ ID NO: 15) antibody stains human tissue sections. Positive staining can be observed in tissue from human foetus hands and human foetus gut system. H7 (comprising $V_L$ of SEQ ID NO: 14 and $V_H$ of SEQ ID NO: 15) antibody does not stain mouse tissue sections. Scale bar: 200 µm.

The results are shown in FIG. 6. Please note that the left hand panel of FIG. 6 shows decreasing concentrations of B3-hFc, whereas the right hand panel shows increasing concentrations of B10-hFc. The signal of B3-hFc were decreasing with decreasing concentration. The signal of B10-hFc were increasing with increasing concentration (FIG. 6).

Conclusion

201F9 binds hYKL-40 at a different epitope than B3 (SEQ ID NO: 3)-hFc or B10 (SEQ ID NO: 4)-hFc.

Example 7: Epitope Mapping of B3 Antibody

Aim:

To identify the epitopes of the B3 (SEQ ID NO: 3) antibody.

Material and Methods:

Epitope mapping of B3 (SEQ ID NO: 3) antibody was performed using linear peptide arrays as described in Geysen et al. Peptides were synthesized as mimics. Peptides were either 15-mers with 14 amino acid overlap, an additional set of 10-mers, looped 8-mers, helical-stabilized peptides of 19 amino acid length or continuous beta-turn mimics of 20 amino acid length.

Relative binding response of 0.1 µg/mL B3-mFc compared to 0.5 µg/ml Mouse IgG1 S1A1 of each peptide was analyzed. The cut-off criteria were at least 10-fold signal over control and at least two peptides in a peak.

Results and Conclusion

The following sequences were identified using the criteria indicated above: amino acids 46-58 or 76-127 or 192-203 or 213-225 or 234-247 or 250-269 or 274-286 or 294-314 or 359-373 of SEQ ID NO: 1. The epitope of B3 is thus believed to comprise or be positioned within the aforementioned sequences.

Example 8: Epitope Mapping of B10 Antibody

Aim:

To identify the epitopes of the B10 (SEQ ID NO: 4) antibody.

Material and Methods:

Epitope mapping of B10 (SEQ ID NO: 4) antibody was performed using linear peptide arrays as described in Geysen et al. Peptides were synthesized as mimics. Peptides were either 15-mers with 14 amino acid overlap, an additional set of 10-mers, looped 8-mers, helical-stabilized peptides of 19 amino acid length or continuous beta-turn mimics of 20 amino acid length.

Relative binding response of 0.1 µg/mL B10-mFc compared to 0.5 µg/ml Mouse IgG1 S1A1 of each peptide was analyzed. The cut-off criteria were at least 10-fold signal over control and at least two peptides in a peak.

Results and Conclusion

The following sequences were identified using the criteria indicated above: amino acids 76-92 or 99-131 or 134-158 or 161-182 or 212-225 or 240-263 or 275-286 or 303-324 or 326-348 of SEQ ID NO: 1. The epitope of B10 is thus believed to comprise or be positioned within the aforementioned sequences.

Example 9: Epitope Mapping of H7 Antibody

Aim:

To identify the epitopes of the H7 (SEQ ID NO: 14 and SEQ ID NO: 15) antibody.

Material and Methods:

Epitope mapping of H7 (SEQ ID NO: 14 and SEQ ID NO: 15) antibody was performed using linear peptide arrays as described in Geysen et al. Peptides were synthesized as mimics. Peptides were either 15-mers with 14 amino acid overlap, an additional set of 10-mers, looped 8-mers, helical-stabilized peptides of 19 amino acid length or continuous beta-turn mimics of 20 amino acid length.

Relative binding response of 0.1 µg/mL H7-hFc compared to 0.18 µg/ml Hu IgG1 MA16 MY 1804 of each peptide was analyzed. The cut-off criteria were at least 2-fold signal over control and at least two peptides in a peak.

Results and Conclusion

The following sequences were identified using the criteria indicated above: Epitopes of H7 are comprising or positioned within a sequence selected from amino acids 123-130 or 218-224 or 259-265 or 269-286 or 303-315 of SEQ ID NO: 1. The epitope of H7 is thus believed to comprise or be positioned within the aforementioned sequences.

Example 10

H7 Binds Human YKL-40

Human tissue sections obtained from human foetus hands and human foetus gut system were stained with H7 antibody according to standard immunohistochemical methods. The H7 antibody comprises a $V_L$ of SEQ ID NO: 14 and a $V_H$ of SEQ ID NO: 15 fused to human Fc regions. Positive staining was observed in tissue from human foetus hands and human foetus gut system The staining pattern corresponds to the pattern observed with other antibodies binding human YKL-40 indicating that H7 indeed binds human YKL-40. However, the H7 antibody did not stain mouse tissue sections to any significant extent.

In addition an ELISA experiment was done essentially as described in Example 1, with the following amendments: the ELISA plates were coated with either 2.5 µg/mL human YKL-40 or 2.5 µg/mL murine YKL-40.

H7 antibody comprising a $V_L$ of SEQ ID NO: 14 and a $V_H$ of SEQ ID NO: 15 fused to human Fc regions was used as primary antibody. This antibody is also referred to as H7-hFc herein. A dilution series of the antibody was prepared with the following concentrations:

1: 20 ug/ml
2: 15 ug/ml
3: 12.5 ug/ml
4: 6.25 ug/ml
5: 2.5 ug/ml
6: 1 ug/ml
7: 0.5 ug/ml
8: 0.25 ug/ml

As secondary antibody an anti-human HRP conjugate was used. H7 binds human YKL-40 in a dose dependent manner, and to a lesser extent to murine YKL-40 in an ELISA assay.

```
Sequence overview
Human YKL-40 also known as Chitinase-3-like protein 1 (CHI3L1)
                                                       SEQ ID NO: 1
MGVKASQTGFVVLVLLQCCSAYKLVCYYTSWSQYREGDGSCFPDALDRFLCTHIIYSFANI

SNDHIDTWEWNDVTLYGMLNTLKNRNPNLKTLLSVGGWNFGSQRFSKIASNTQSRRTFIK

SVPPFLRTHGFDGLDLAWLYPGRRDKQHFTTLIKEMKAEFIKEAQPGKKQLLLSAALSAGK

VTIDSSYDIAKISQHLDFISIMTYDFHGAWRGTTGHHSPLFRGQEDASPDRFSNTDYAVGY

MLRLGAPASKLVMGIPTFGRSFTLASSETGVGAPISGPGIPGRFTKEAGTLAYYEICDFLRG

ATVHRILGQQVPYATKGNQWVGYDDQESVKSKVQYLKDRQLAGAMVWALDLDDFQGSF

CGQDLRFPLTNAIKDALAAT

Murine YKL-40
                                                       SEQ ID NO: 2
MHTSTEARMGMRAALTGFAVLMLLQSCSAYKLVCYFTSWSQYREGVGSFLPDAIQPFLCT

HIIYSFANISSDNMLSTWEWNDESNYDKLNKLKTRNTNLKTLLSVGGWKFGEKRFSEIASN

TERRTAFVRSVAPFLRSYGFDGLDLAWLYPRLRDKQYFSTLIKELNAEFTKEVQPGREKLL

LSAALSAGKVAIDTGYDIAQIAQHLDFINLMTYDFHGVWRQITGHHSPLFQGQKDTRFDRY

SNVNYAVQYMIRLGAQASKLLMGIPTFGKSFTLASSENQLGAPISGEGLPGRFTKEAGTLA

YYEICDFLKGAEVHRLSNEKVPFATKGNQWVGYEDKESVKNKVGFLKEKKLAGAMVWAL

DLDDFQGTCQPKEFFPLTNAIKDALA

B3 predator
                                                       SEQ ID NO: 3
MAEVQLLESGGGLVQPGGSLRLSCAASGFRDSDEDMGWVRQAPGKGLEWVSSISAPGG

STYYADSVKGRFTISRDNSKNTLYLQMNSLRAEDTAVYYCASHYNYGHWFDYWGQGTLV

TVSSAA

B10 predator
                                                       SEQ ID NO: 4
MAEVQLLESGGGLVQPGGSLRLSCAASGFRDSDEDMGWVRQAPGKGLEWVSSISADSG

STYYADSVKGRFTISRDNSKNTLYLQMNSLRAEDTAVYYCASDYNYWYWFDYWGQGTLV

TVSSAA

B3 CDR1
                                                       SEQ ID NO: 5
GFRDSDEDMG
```

-continued

B3 CDR2  
SEQ ID NO: 6  
ISAPGGSTYYADSVKG

B3 CDR3  
SEQ ID NO: 7  
HYNYGHWFDY

B10 CDR1  
SEQ ID NO: 8  
GFRDSDEDMG

B10 CDR2  
SEQ ID NO: 9  
ISADSGSTYYADSVKG

B10 CDR3  
SEQ ID NO: 10  
DYNYWYWFDY

CDR1 general formula  
SEQ ID NO: 11  
GFRDSDEDMG

CDR2 general formula  
SEQ ID NO: 12  
ISAXXGSTYYADSVKG

CDR3 general formula  
SEQ ID NO: 13  
XYNYXXWFDY

H7 light  
SEQ ID NO: 14  
DIQMTQSPASLSASVGETVTITCGASENIYGALNWYQRKQGKSPQLLIYGATTLADGMSSR

FSGSGSGRQYSLKISSLHPDDVATYYCQNVLTTPWTFGGGTKLEIKTVAAPSVFIFPPSDE

QLKSGTASVVCLLNNFYPREAKVQWKVDNALQSGNSQESVTEQDSKDSTYSLSSTLTLSK

ADYEKHKVYACEVTHQGLSSPVTKSFNRGEC

H7 heavy  
SEQ ID NO: 15  
EVQLQQSGAELVKPGASVKLSCTASGFNIKDTYMHWVKQRPEQGLEWIGRIDPANGNTIY

ASKFQGKATITRDTSSNTAYMQLSSLTSGDTAVYYCTRGVYYYGGSFYAMDYWGQGTSV

TVSSAASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

H7 CDR1 light  
SEQ ID NO: 16  
GASENIYGALN

H7 CDR2 light  
SEQ ID NO: 17  
GATTLAD

H7 CDR3 light  
SEQ ID NO: 18  
QNVLTTPWT

H7 CDR1 heavy  
SEQ ID NO: 19  
GFNIKDT

H7 CDR2 heavy  
SEQ ID NO: 20  
DPANGN

-continued

H7 CDR3 heavy
SEQ ID NO: 21
GVYYYGGSFYAMDY hFc1
SEQ ID NO: 22
DKTHTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK hFc2
SEQ ID NO: 23
VECPPCPAPPVAGPSVFLFPPKPKDTLMISRTPEVTCVVVDVSHEDPEVQFNWYVDGMEV
HNAKTKPREEQFNSTFRVVSVLTVVHQDWLNGKEYKCKVSNKGLPAPIEKTISKTKGQPR
EPQVYTLPPSREEMTKNQVSLTCLVKGFYPSDIAVEWESNGQPENNYKTTPPMLDSDGSF
FLYSKLTVDKSRWQQGNVFSCSVMHEALHNHYTQKSLSLSPGK CDR1 of disclosed YKL-40 antibody
SEQ ID NO: 24
FRDSDEDMG

CDR2.1
SEQ ID NO: 25
SIGDESGSTYYADSV

CDR2.2
SEQ ID NO: 26
SINAPDGSTYYADSV

CDR2.3
SEQ ID NO: 27
SISGSDGSTYYADSV

CDR2.4
SEQ ID NO: 28
SINNSGGSTYYADSV

CDR2.5
SEQ ID NO: 29
SISAESGSTYYADSV

CDR2.6
SEQ ID NO: 30
SINYNSGSTYYADSV

CDR2.7
SEQ ID NO: 31
SISDEDGSTYYADSV

CDR2.8
SEQ ID NO: 32
SISGESGSTYYADSV

CDR2.9
SEQ ID NO: 33
SIQSSDGSTYYADSV

CDR2.10
SEQ ID NO: 34
SINNESGSTYYADSV

CDR2.11
SEQ ID NO: 35
SIYAPNGSTYYADSV

CDR2.12
SEQ ID NO: 36
SIASDSGSTYYADSV

CDR2.13
SEQ ID NO: 37
SIGAGSGSTYYADSV

-continued

```
CDR2.14                                             SEQ ID NO: 38
SINANDGSTYYADSV

CDR2.15                                             SEQ ID NO: 39
SIGNYNGSTYYADSV

CDR2.16                                             SEQ ID NO: 40
SIYGPSGSTYYADSV

CDR2.17                                             SEQ ID NO: 41
SIDAEDGSTYYADSV

CDR3.1                                              SEQ ID NO: 42
TSDSYWSFDY

CDR3.2                                              SEQ ID NO: 43
QWDDGYAFDY

CDR3.3                                              SEQ ID NO: 44
TDYLRSSFDY

CDR3.4                                              SEQ ID NO: 45
TYDWNYSFDY

CDR3.5                                              SEQ ID NO: 46
QYGAYHDFDY

CDR3.6                                              SEQ ID NO: 47
TPNLNSSFDY

CDR3.7                                              SEQ ID NO: 48
SGDWWYGFDY

CDR3.8                                              SEQ ID NO: 49
VDPLDTYFDY

CDR3.9                                              SEQ ID NO: 50
SSQNGYVFDY

CDR3.10                                             SEQ ID NO: 51
TSYYGFDFDY

CDR3.11                                             SEQ ID NO: 52
NTYDAFDY

CDR3.12                                             SEQ ID NO: 53
SGYAGTVFDY

CDR3.13                                             SEQ ID NO: 54
STDARWQFDY

CDR3.14                                             SEQ ID NO: 55
QYDDEFAFDY

CDR3.15                                             SEQ ID NO: 56
VSDSGFSFDY

CDR3.16                                             SEQ ID NO: 57
SDWDGYSFDY
```

```
CDR3.17
                                                         SEQ ID NO: 58
QDGAYYTFDY

CDR2.18
                                                         SEQ ID NO: 59
SISTSDGSTYY

CDR3.18
                                                         SEQ ID NO: 60
QYDTGYSFDY

IgE
                                                         SEQ ID NO: 61
STQSPSVFPLTRCCKNIPSNATSVTLGCLATGYFPEPVMVTWDTGSLNGTTMTLPATTLTL

SGHYATISLLTVSGAWAKQMFTCRVAHTPSSTDWVDNKTFSVCSRDFTPPTVKILQSSCD

GGGHFPPTIQLLCLVSGYTPGTINITWLEDGQVMDVDLSTASTTQEGELASTQSELTLSQK

HWLSDRTYTCQVTYQGHTFEDSTKKCADSNPRGVSAYLSRPSPFDLFIRKSPTITCLVVDL

APSKGTVNLTWSRASGKPVNHSTRKEEKQRNGTLTVTSTLPVGTRDWIEGETYQCRVTH

PHLPRALMRSTTKTSGPRAAPEVYAFATPEWPGSRDKRTLACLIQNFMPEDISVQWLHNE

VQL mFc
                                                         SEQ ID NO: 62
RSPPLKECPPCAAPDLLGGPSVFIFPPPKIKDVLMISLSPMVTCVVVDVSEDDPDVQISWFVN

NVEVHTAQTQTHREDYNSTLRVVSALPIQHQDWMSGKEFKCKVNNRALPSPIEKTISKPR

GPVRAPQVYVLPPPAEEMTKKEFSLTCMITGFLPAEIAVDWTSNGRTEQNYKNTATVLDS

DGSYFMYSKLRVQKSTWERGSLFACSVVHEGLHNHLTTKTISRSLGK
```

REFERENCES

Böckelmann L, Starzonek C, Niehoff A C, Karst U, Thomale J, Schlüter H, Bokemeyer C, Aigner A, Schumacher U. Detection of doxorubicin, cisplatin and therapeutic antibodies in formalin-fixed paraffin-embedded human cancer cells. Histochem Cell Biol. 2020 May; 153 (5): 367-377. doi: 10.1007/s00418-020-01857-x. Epub 2020 Mar. 3. PMID: 32125512; PMCID: PMC7225197.

Brockmann E C, Akter S, Savukoski T, Huovinen T, Lehmusvuori A et al. (2011) Synthetic single-framework antibody library integrated with rapid affinity maturation by VL shuffling. Protein Eng Des Sel 24:691-700. doi: 10.1093/protein/gzr023. PubMed: 21680620.

Christ D, Famm K, Winter G (2007) Repertoires of aggregation resistant human antibody domains. Protein Eng Des Sel 20:413-416. doi: 10.1093/protein/gzm037. PubMed: 17720749.

Fellouse F A, Esaki K, Birtalan S, Raptis D, Cancasci V J et al. (2007) High-throughput generation of synthetic antibodies from highly functional minimalist phage-displayed libraries. J Mol Biol 373:924-940. doi: 10.1016/j.jmb.2007.08.005. PubMed: 17825836.

Ferretti S, Allegrini P R, Becquet M M, McSheehy P M. Tumor interstitial fluid pressure as an early-response marker for anticancer therapeutics. Neoplasia. 2009 September; 11 (9): 874-81.

Hust M, Dübel S (2004) Mating antibody phage display with proteomics. Trends Biotechnol 22:8-14. doi: 10.1016/j.tibtech.2003.10.011. PubMed: 14690617.

Jones, P., Dear, P., Foote, J. et al. Replacing the complementarity-determining regions in a human antibody with those from a mouse. Nature 321, 522-525 (1986). https://doi.org/10.1038/321522a0

Karahan Z S, Aras M, Sütlü T. TCR-NK Cells: A Novel Source for Adoptive Immunotherapy of Cancer. Turk J Haematol. 2023 Feb. 28; 40 (1): 1-10. doi: 10.4274/tjh.galenos.2022.2022.0534. Epub 2023 Jan. 31. PMID: 36719099; PMCID: PMC9979742.

Melero, I., Berman, D., Aznar, M. et al. Evolving synergistic combinations of targeted immunotherapies to combat cancer. Nat Rev Cancer 15, 457-472 (2015). https://doi.org/10.1038/nrc3973

Mandrup, O. A., N. A. Friis, S. Lykkemark, J. Just and P. Kristensen (2013). "A novel heavy domain antibody library with functionally optimized complementarity determining regions." PLoS One 8 (10): e76834.

Morrison S L, Johnson M J, Herzenberg L A, Oi V T. Chimeric human antibody molecules: mouse antigen-binding domains with human constant region domains. Proc Natl Acad Sci USA. 1984 November; 81 (21): 6851-5. doi: 10.1073/pnas.81.21.6851.

Moutel, S., A. El Marjou, O. Vielemeyer, C. Nizak, P. Benaroch, S. Dubel and F. Perez (2009). "A multi-Fc-species system for recombinant antibody production." BMC Biotechnol 9:14.

Pansri P, Jaruseranee N, Rangnoi K, Kristensen P, Yamabhai M (2009) A compact phage display human scFv library for selection of antibodies to a wide variety of antigens. BMC Biotechnol 9:6. doi: 10.1186/1472-6750-9-6. PubMed: 19175944.

Rothe C, Urlinger S, Löhning C, Prassler J, Stark Y et al. (2008) The human combinatorial antibody library HuCAL GOLD combines diversification of all six CDRs according to the natural immune system with a novel display method for efficient selection of high-affinity antibodies. J Mol Biol 376:1182-1200. doi: 10.1016/j.jmb.2007.12.018. PubMed: 18191144.

Silacci M, Brack S, Schirru G, Mårlind J, Ettorre A et al. (2005) Design, construction, and characterization of a large synthetic human antibody phage display library. Proteomics 5:2340-2350. doi: 10.1002/pmic.200401273. PubMed: 15880779.

Wang, Q. et al. Design and Production of Bispecific Antibodies. Antibodies 8, 43 (2019).

The invention claimed is:

1. A composition comprising one or more antibodies specifically binding YKL-40, wherein at least one of the antibodies comprises at least one variable region comprising a CDR1, CDR2 and CDR3, wherein, a) CDR1 comprises amino acid sequence SEQ ID NO:5;
CDR2 comprises amino acid sequence SEQ ID NO: 6; and
CDR3 comprises amino acid sequence SEQ ID NO: 7;
or b) CDR1 comprises amino acid sequence SEQ ID NO: 8;
CDR2 comprises amino acid sequence SEQ ID NO: 9; and
CDR3 comprises amino acid sequence SEQ ID NO: 10;
or c) at least one antibody comprises a light chain variable region and a heavy chain variable region, each comprising a CDR1, CDR2 and CDR3, wherein:
CDR1 of the light chain variable region comprises amino acid sequence SEQ ID NO: 16;
CDR2 of the light chain variable region comprises amino acid sequence SEQ ID NO: 17;

CDR3 of the light chain variable region comprises amino acid sequence SEQ ID NO: 18;
CDR1 of the heavy chain variable region comprises amino acid sequence SEQ ID NO: 19;
CDR2 of the heavy chain variable region comprises amino acid sequence SEQ ID NO: 20; and
CDR3 of the heavy chain variable region comprises amino acid sequence SEQ ID NO: 21.

2. The composition according to claim 1, wherein the composition comprises two antibodies specifically binding YKL-40, wherein a first antibody of the two antibodies comprises the CDR1, CDR2, and CDR3 of a), and a second antibody of the two antibodies comprises the CDR1, CDR2, and CDR3 of b) or the CDR1, CDR2, and CDR3 of the light chain variable region and the CDR1, CDR2, and CDR3 of the heavy chain variable region of c); or wherein the first antibody of the two antibodies comprises the CDR1, CDR2, and CDR3 of b), and the second antibody of the two antibodies comprises the CDR1, CDR2, and CDR3 of a) or the CDR1, CDR2, and CDR3 of the light chain variable region and the CDR1, CDR2, and CDR3 of the heavy chain variable region of c), or wherein the first antibody of the two antibodies comprises the CDR1, CDR2, and CDR3 of the light chain variable region and the CDR1, CDR2, and CDR3 of the heavy chain variable region of c), and the second antibody of the two antibodies comprises the CDR1, CDR2, and CDR3 of a) and b).

3. The composition according to claim 1, wherein at least one antibody specifically binding YKL-40 comprises a variable region comprising a CDR1, CDR2 and CDR3, wherein,
CDR1 comprises the amino acid sequence of SEQ ID NO:5;
CDR2 comprises the amino acid sequence of SEQ ID NO: 6; and
CDR3 comprises the amino acid sequence of SEQ ID NO: 7.

4. The composition according to claim 1, wherein at least one antibody specifically binding YKL-40 comprises a variable region comprising a CDR1, CDR2 and CDR3, wherein,
CDR1 comprises the amino acid sequence of SEQ ID NO: 8;
CDR2 comprises the amino acid sequence of SEQ ID NO: 9; and
CDR3 comprises the amino acid sequence of SEQ ID NO: 10.

5. The composition according to claim 1, wherein at least one antibody specifically binding YLK-40 comprises a variable region comprising the amino acid sequence of SEQ ID NO:3 or SEQ ID NO:4.

6. The composition according to claim 1, wherein the variable region(s) are linked to an Fc region.

7. The composition according to claim 1, wherein at least one antibody specifically binding YKL-40 comprises variable regions comprising a CDR1, CDR2 and CDR3, wherein,
CDR1 of the light chain variable region comprises the amino acid sequence of SEQ ID NO: 16;
CDR2 of the light chain variable region comprises the amino acid sequence of SEQ ID NO: 17;
CDR3 of the light chain variable region comprises the amino acid sequence of SEQ ID NO: 18;
CDR1 of the heavy chain variable region comprises the amino acid sequence of SEQ ID NO: 19;
CDR2 of the heavy chain variable region comprises the amino acid sequence of SEQ ID NO: 20; and
CDR3 of the heavy chain variable region comprises the amino acid sequence of SEQ ID NO: 21.

8. The composition according to claim 1, wherein at least one antibody specifically binding YLK-40 comprises a light chain variable region comprising the amino acid sequence of SEQ ID NO: 14 and a heavy chain variable region comprising the amino acid sequence of SEQ ID NO:15.

9. The composition according to claim 1, wherein the at least one antibody specifically binding YKL-40 is capable of binding an epitope present in both human and murine YKL-40.

10. The composition according to claim 1, wherein the composition comprises one antibody with a variable region comprising a CDR1, CDR2 and CDR3, wherein,
CDR1 comprises the amino acid sequence of SEQ ID NO:5;
CDR2 comprises the amino acid sequence of SEQ ID NO: 6; and
CDR3 comprises an amino acid sequence of SEQ ID NO: 7;
and another antibody with a variable region comprising a CDR1, CDR2 and CDR3, wherein,
CDR1 comprises the amino acid sequence of SEQ ID NO: 8;
CDR2 comprises the amino acid sequence of SEQ ID NO: 9; and
CDR3 comprises the amino acid sequence of SEQ ID NO: 10.

11. The composition according to claim 1, wherein the composition comprises one antibody comprising a variable region comprising a CDR1, CDR2 and CDR3, wherein,
CDR1 comprises the amino acid sequence of SEQ ID NO: 5;
CDR2 comprises the amino acid sequence of SEQ ID NO: 6; and
CDR3 comprises the amino acid sequence of SEQ ID NO: 7;
and another antibody comprising a light chain variable region and a heavy chain variable region each comprising a CDR1, CDR2 and CDR3, wherein, CDR1 of the light chain variable region comprises an amino acid sequence of SEQ ID NO: 16;
CDR2 of the light chain variable region comprises the amino acid sequence of SEQ ID NO: 17;
CDR3 of the light chain variable region comprises the amino acid sequence of SEQ ID NO: 18;
CDR1 of the heavy chain variable region comprises the amino acid sequence of SEQ ID NO: 19;
CDR2 of the heavy chain variable region comprises the amino acid sequence of SEQ ID NO: 20; and
CDR3 of the heavy chain variable region comprises the amino acid sequence of SEQ ID NO: 21.

12. The composition according to claim 1, wherein the composition comprises one antibody comprising a variable region comprising a CDR1, CDR2 and CDR3, wherein,
CDR1 comprises the amino acid sequence of SEQ ID NO: 8;
CDR2 comprises the amino acid sequence of SEQ ID NO: 9; and
CDR3 comprises the amino acid sequence of SEQ ID NO: 10;
and another antibody comprising variable regions comprising a CDR1, CDR2 and CDR3, wherein, CDR1 of the light chain variable region comprises the amino acid sequence of SEQ ID NO: 16;
CDR2 of the light chain variable region comprises the amino acid sequence of SEQ ID NO: 17;
CDR3 of the light chain variable region comprises the amino acid sequence of SEQ ID NO: 18;

CDR1 of the heavy chain variable region comprises the amino acid sequence of SEQ ID NO: 19;

CDR2 of the heavy chain variable region comprises the amino acid sequence of SEQ ID NO: 20; and CDR3 of the heavy chain variable region comprises the amino acid sequence of SEQ ID NO: 21.

13. The composition according to claim 1, wherein the composition comprises a bi- or multispecific antibody comprising variable regions specifically binding YKL-40, wherein a first variable region of the bi- or multispecific antibody comprises the CDR1, CDR2, and CDR3 of a), and a second variable region of the bi- or multispecific antibody comprises the CDR1, CDR2, and CDR3 of b) or the CDR1, CDR2, and CDR3 of the light chain variable region and the CDR1, CDR2, and CDR3 of the heavy chain variable region of c); or wherein the first variable region comprises the CDR1, CDR2, and CDR3 of b), and the second variable region comprises the CDR1, CDR2, and CDR3 of a) or the CDR1, CDR2, and CDR3 of the light chain variable region and the CDR1, CDR2, and CDR3 of the heavy chain variable region of c), or wherein the first variable region comprises the CDR1, CDR2, and CDR3 of the light chain variable region and the CDR1, CDR2, and CDR3 of the heavy chain variable region of c), and the second variable region comprises the CDR1, CDR2, and CDR3 of a) and b).

14. The composition according to claim 13, wherein the bi- or multispecific antibody comprises one or more variable regions comprising a CDR1 comprising the amino acid sequence SEQ ID NO: 5, a CDR2 comprising the amino acid sequence SEQ ID NO: 6 and a CDR3 comprising the amino acid sequence SEQ ID NO:7 and one or more variable regions comprising a CDR1 comprising the amino acid sequence SEQ ID NO: 8, a CDR2 comprising the amino acid sequence of SEQ ID NO: 9 and a CDR3 comprising the amino acid sequence of SEQ ID NO:10.

15. The composition according to claim 1, wherein at least one antibody specifically binding YKL-40 comprises a variable region comprising a CDR1, CDR2 and CDR3, wherein, CDR1 consists of the amino acid sequence of SEQ ID NO:5;

CDR2 consists of the amino acid sequence of SEQ ID NO: 6; and

CDR3 consists of the amino acid sequence of SEQ ID NO: 7.

16. The composition according to claim 1, wherein at least one antibody specifically binding YKL-40 comprises a variable region comprising a CDR1, CDR2 and CDR3, wherein, CDR1 consists of the amino acid sequence of SEQ ID NO: 8;

CDR2 consists of the amino acid sequence of SEQ ID NO: 9; and

CDR3 consists of the amino acid sequence of SEQ ID NO: 10.

* * * * *